United States Patent

Kitaguchi et al.

Patent Number: 4,729,936
Date of Patent: Mar. 8, 1988

[54] IMAGE FORMING PROCESS INCLUDING A HEATING STEP

[75] Inventors: Hiroshi Kitaguchi; Kozo Sato; Masatoshi Kato, all of Kanagawa, Japan

[73] Assignee: Fuji Photo Film Co., Ltd., Kanagawa, Japan

[21] Appl. No.: 867,176

[22] Filed: May 27, 1986

[30] Foreign Application Priority Data

May 24, 1985 [JP] Japan .................. 60-111596

[51] Int. Cl.[4] .................. G03C 5/26; G03C 5/34; G03C 5/54; G03C 1/00
[52] U.S. Cl. .................. 430/151; 430/203; 430/350; 430/617; 430/955; 430/957; 430/959; 430/960
[58] Field of Search .............. 430/151, 203, 350, 957, 430/959, 960, 617

[56] References Cited

FOREIGN PATENT DOCUMENTS 0187343 7/1986 European Pat. Off. .......... 430/955

*Primary Examiner*—Paul R. Michl
*Assistant Examiner*—Mark R. Buscher
*Attorney, Agent, or Firm*—Sughrue, Mion, Zinn, Macpeak, and Seas

[57] ABSTRACT

An image forming process including a heating step is disclosed. The process comprises conducting said heating step in the presence of at least one compound represented by formula (I), (II), or (III).

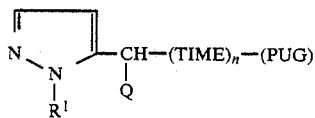

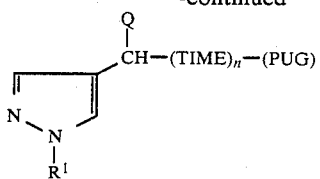

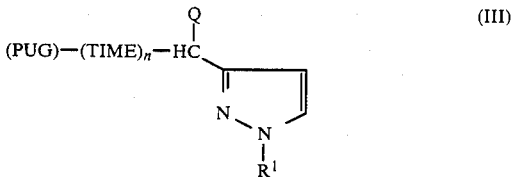

wherein $R^1$ represents

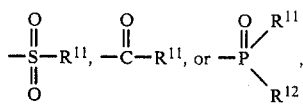

wherein $R^{11}$ and $R^{12}$ each represents a substituted or unsubstituted alkyl group, a substituted or unsubstituted cycloalkyl group, a substituted or unsubstituted alkenyl group, a substituted or unsubstituted aralkyl group, a substituted or unsubstituted aryl group, a substituted or unsubstituted heterocyclic group, a substituted or unsubstituted alkyloxy group, a substituted or unsubstituted aryloxy group, a substituted or unsubstituted alkylthio group, a substituted or unsubstituted arylthio group or a substituted or unsubstituted amino group; $R^{11}$ and $R^{12}$ together form a 5-membered or 6-membered ring; Q represents a hydrogen atom or a substituted or unsubstituted alkyl group, a substituted or unsubstituted cycloalkyl group, or a substituted or unsubstituted aryl group, or Q represents a group linked to the pyrazole ring, TIME or PUG either directly or through another atom to form a ring; TIME represents a timing group; PUG represents a photographically useful group; and n represents 0 or a positive integer.

The image forming process provides for little variation in photographic characteristics even when there is a substantial variation in the heat-processing temperature.

8 Claims, No Drawings

IMAGE FORMING PROCESS INCLUDING A HEATING STEP

FIELD OF THE INVENTION

The present invention relates to an image forming process involving a heating step, and, more particularly, to an image forming process including a heating step which is associated with the use of a precursor of a photographically useful reagent.

BACKGROUND OF THE INVENTION

Silver halide photography is superior to other photographic methods, such as electrophotography and diazo photography, in the photographic characteristics that can be achieved, such as sensitivity and tone control, and has, therefore, been used most widely. Recent years have witnessed development of technology for producing an image more easily and quickly by employing a heat-developing process, not relying on the use of a developer solution, in lieu of the conventional wet process which involves the use of developer and other solutions in the neighborhood of room temperature for the processing of a silver halide light-sensitive material.

The heat-developable light-sensitive material is known in this field of art and examples of such material and the process involved are described in the literature such as *The Fundamentals of Photographic Engineering*, pp. 553–555 Corona-Sha, (1979), *Image Information*, p. 40 (April, 1978); *Neblette's Handbook of Photography and Reprography*, 7th Ed., pp. 32–33 Van Nostrand Reinhold Company, (1977). U.S. Pat. Nos. 3,152,904, 3,301,678, 3,392,020 and 3,457,075, British Pat. Nos. 1,131,108 and 1,167,777 and *Research Disclosure* pp. 9–15, (RD 17029) (June, 1978).

For the formation of color images by heat-development, a variety of processes have been proposed.

Regarding the formation of a color image through the coupling reaction between an oxidized developing agent and a coupler, U.S. Pat. No. 3,531,286 teaches the use of p-phenylenediamine type reducing agents and phenolic or active methylene type couplers; U.S. Pat. No. 3,761,270 describes p-aminophenol type reducing agents; Belgian Pat. No. 802,519 and *Research Disclosure* p. 31–32 (September, 1975) describe sulfonamidophenol type couplers; and U.S. Pat. No. 4,021,240 describes the combination of sulfonamidophenol type reducing agents with four-equivalent couplers.

Regarding the technology of forming a positive color image by the photosensitive silver dye bleach method, *Research Disclosure* pp. 30–32, (RD-14433) (April, 1976), *Research Disclosure* pp. 14–15, (RD-15227) (December, 1976, and U.S. Pat. No. 4,235,957, among others, describe useful dyes and bleaching methods.

The methods for forming an image by heat-development comprising the utilization of a compound having a built-in dye moiety and adapted to release a dye either in correspondence or in reverse correspondence with the reduction of silver halide to silver are described in European Laid-Open Patent No. 76,492 and No. 79,056 and Japanese Patent Application (OPI) Nos. 28928/83, 26008/83 (the term "OPI" as used herein refers to a "published unexamined Japanese patent application").

Further, the methods for transferring the mobile dye imagewise formed by heat-development to an image receiving layer under heating and the associated image receiving materials are described in Japanese Patent Application (OPI) Nos. 58543/83, 79247/83 and 168439/84, for instance.

However, in these thermal image forming processes, as the necessary photographic reagents are not supplied from a developer solution or the like, all the photographic reagents required for development must be self-contained within the photographic light-sensitive material itself.

However, if the photographic reagents are added in their active forms to such a photographic light-sensitive material, they may react with the other substances contained in the light-sensitive material or be decomposed under the influences of heat, oxygen, and the like during storage before processing, with the result that they cannot be expected to fully display their designed functions.

One approach toward solving these problems involves blocking the active groups of photographic reagents and incorporating them in substantially inactive forms, namely as "precursors", in the photographic light-sensitive material.

When a photographically useful reagent in a dye, its functional group which would otherwise exert a material influence on its spectral absorption is blocked to shift the spectral absorption of the dye toward the short wavelength side of the long wavelength side. Then, if the dye is present in the same layer as the silver halide emulsion sensitive to the corresponding region of the spectrum, the loss of sensitivity due to the so-called filter effect can be obviated.

When the photographically useful reagent is an antifoggant or a development inhibitor, blocking its active group results in the suppression of its adsorption on the photosensitive silver halide and desensitization due to silver salt formation during storage, and as the photographic reagent is released at an appropriate time, it can be expected to obtain a fog without sacrificing the sensitivity, inhibition of fogging due to over-development, and termination of development at the appropriate time.

When the photographically useful reagent is a developing agent, a development auxiliary agent or a coupler, masking its active group or adsorbent group enables prevention of photographically undesirable influences due to formation of a semiquinone or oxide and prevents generation of fog nuclei during storage through prevention of the influx of electrons into silver halide, thus contributing to stable processing.

When the photographically useful reagent is a bleaching accelerator or a bleach-fix accelerator, too, blocking its active group leads to the advantage that the reaction thereof with other concomitant substances is inhibited during storage while the expected function of the reagent may be deployed to advantage by unblocking during processing.

Regarding such technology for blocking photographically useful reagents, several specific procedures are known in the field of conventional photographic light-sensitive materials. For example, the prior art includes the use of acyl or sulfonyl groups as a blocking or masking group as described in Japanese Patent Publication No. 44,805/72, the use of blocking groups such that photographically useful groups are released by the so-called reverse Michael reaction as taught in Japanese Patent Publication Nos. 17369/79, 9696/80 and 34927/80, the use of a blocking group such that a photographic reagent is released in timed relation with the formation of a quinonemethide or quinonemethide-like compound through intramolecular electron transfer as described in Japanese Patent Publication No. 39727/79, Japanese Patent Application (OPI) Nos. 135944/82, 135945/82 and 136640/82, the utilization of an intramolecular cyclization reaction as described in Japanese Patent Application (OPI) No. 53330/80, and the use of a ring-opening reaction of a 5-membered or 6-membered ring system as described in Japanese Patent Application (OPI) Nos. 76541/82, 135949/82 and 179842/82.

However, these known techniques invariably utilize hydrolysis or deprotonation due to the action of OH⁻ in wet development at or near room temperature and useful precursor technology has not been known in the field of heat development (also referred to as thermal development) using an organic base.

SUMMARY OF THE INVENTION

The object of the present invention is to provide an image forming method including a heating step which provides for little variation in photographic characteristics even when there is a substantial variation in heat-processing temperature by a novel photographically useful reagent precursor technology employing a compound which is stable at room temperature and adapted to release a photographically useful reagent only at a heat-development or heat-transfer stage.

The above objects have been accomplished by the present invention, which is directed to an image forming process involving a heating step which is conducted in the presence of at least one compound represented by formula (I), (II), or (III).

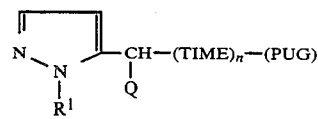
(I)

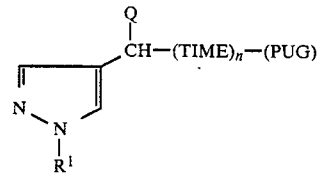
(II)

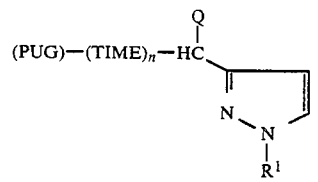
(III)

In the above formulae (I), (II), and (III), $R^1$ represents

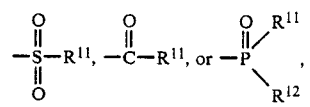

wherein $R^{11}$ and $R^{12}$ (which may be the same or different) each represents a substituted or unsubstituted alkyl group, a substituted or unsubstituted, cycloalkyl group, a substituted or unsubstituted alkenyl group, a substituted or unsubstituted aralkyl group, a substituted or unsubstituted aryl group, a substituted or unsubstituted heterocyclic group, a substituted or unsubstituted alkyloxy group, a substituted or unsubstituted aryloxy group, a substituted or unsubstituted alkylthio group, a substituted or unsubstituted arylthio group or a substituted or unsubstituted amino group, or $R^{11}$ and $R^{12}$ together form a 5-membered or 6-membered ring; Q represents a hydrogen atom or a substituted or unsubstituted alkyl group, a substituted or unsubstituted cycloalkyl group or a substituted or unsubstituted aryl group, or Q represents a group linked to the pyrazole ring, TIME, or PUG either directly or through another atom to form a ring; TIME represents a timing group; PUG represents a photographically useful group; and n represents 0 or a positive integer.

DETAILED DESCRIPTION OF THE INVENTION

The implementation of the present invention will hereinafter be described in detail.

In the image forming process including a heating step of the present invention, said heating step is conducted in the presence of at least one compound represented by formulae (I), (II), and (III).

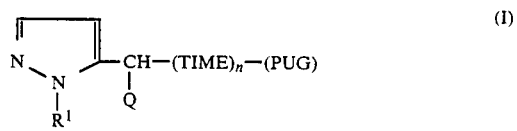
(I)

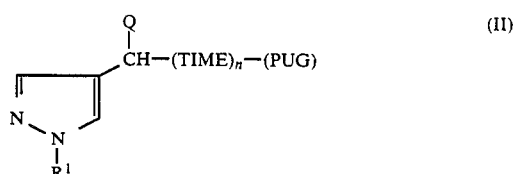
(II)

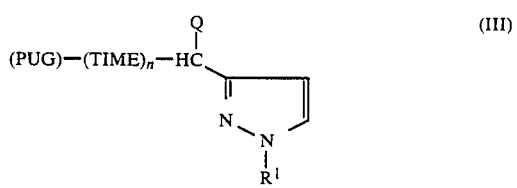
(III)

In the above formulae (I) through (III), $R^1$ represents formula (A), (B), or (C).

(A)

(B)

(C)

In the above formulae (A), (B), and (C), $R^{11}$ and $R^{12}$ (which may be the same or different) each represents a substituted or unsubstituted alkyl group, a substituted or unsubstituted cycloalkyl group, a substituted or unsubstituted alkenyl group, a substituted or unsubstituted aralkyl group, a substituted or unsubstituted aryl group, a substituted or unsubstituted heterocyclic group, a substituted or unsubstituted alkyloxy group, a substituted or unsubstituted aryloxy group, a substituted or unsubstituted alkylthio group, a substituted or unsubstituted arylthio group or a substituted or unsubstituted amino group. Alternatively, $R^{11}$ and $R^{12}$ can together form a 5-membered or 6-membered ring. The alkyl group for $R^{11}$ and $R^{12}$ is preferably a straight-chain or branched-chain alkyl group having from 1 to 18 carbon atoms. Specific examples thereof include a methyl group, an ethyl group, a n-propyl group, a n-butyl group, a n-hexyl group, a n-heptyl group, a 2-ethylhexyl group, a n-decyl group, a n-dodecyl group and so on. The cycloalkyl group is preferably a 5-membered or 6-membered cycloalkyl group having from 5 to 10 carbon atoms. Specific examples thereof include a cyclopentyl group, a cyclohexyl group and so on. The substituent on the substituted alkyl or cycloalkyl group includes a halogen atom, an alkoxy group, an aryloxy group, a cyano group, an alkyl- or arylthio group, a disubstituted carbamoyl group, an alkyl- or arylsulfonyl group, an alkyl- or aryl-disubstituted amino group, a carboxy group, a sulfo group, an acylamino group, a sulfonylamino group and so on.

Examples of the alkenyl group include a vinyl group, an aryl group, a crotyl group, and a substituted or unsubstituted styryl group.

Examples of the aralkyl group include a benzyl group and a β-phenethyl group.

The alkenyl or aralkyl group may have substituents such as mentioned for the substituent on the substituted alkyl group.

The preferred aryl group contains from 6 to 18 carbon atoms. Specific examples thereof include a phenyl group, a naphthyl group, an anthryl group and so on. The substituent on the substituted aryl group includes a substituted or unsubstituted alkyl group, a substituted or unsubstituted alkoxy group, a substituted or unsubstituted aryl group, a halogen atom, an acylamino group, a sulfonylamino group, a cyano group, a nitro group, an alkyl- or arylthio group, an alkyl- or arylsulfonyl group, an alkoxycarbonyloxy group, a substituted or unsubstituted carbamoyl group, a substituted or unsubstituted sulfamoyl group, an alkyl- or aryl-disubstituted amino group, a carboxy group, a sulfo group, an alkyl- or aryloxycarbonyl group.

The preferred heterocyclic group is a 5-membered or 6-membered heterocyclic group (the hetero atom or atoms are selected from among O, N, and S). Specific examples thereof include a pyridyl group, a furyl group, a thienyl group, a pyrrolyl group and an indolyl group. This heterocyclic group may have substituents such as mentioned in connection with the above-mentioned substituted aryl group.

Preferred alkyloxy- and aryloxy groups, and alkylthio and arylthio groups, are represented by formulae (D) and (E), respectively.

$$-OR^{13} \quad (D)$$

$$-SR^{14} \quad (E)$$

Preferred examples of $R^{13}$ and $R^{14}$ include the same as those mentioned hereinbefore for the substituted or unsubstituted alkyl or substituted or unsubstituted aryl groups described for $R^{11}$ and $R^{12}$.

The amino groups $R^{11}$ and $R^{12}$ may, for example, be $-NH_2$ or an alkyl or aryl-monosubstituted or disubstituted amino group (e.g. a dimethylamino group, a diethylamino group, etc.).

Q represents a hydrogen atom or a substituted or unsubstituted alkyl group, a substituted or unsubstituted cycloalkyl group, or a substituted or unsubstituted aryl group. Alternatively, Q may be linked to the pyrazole ring, TIME, or PUG either directly or through another atom to form a ring.

Preferred examples of Q include the same groups as those described for the substituted or unsubstituted alkyl, cycloalkyl or aryl group referring to $R^{11}$ and $R^{12}$.

The pyrazole rings of formulae (I), (II), and (III) include those wherein the carbon atoms of the pyrazole ring other than the carbon atom having the substituent

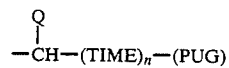

have substituents other than hydrogen atoms.

Preferred examples of such substituent mentioned just above include those described for the substituted aryl group referring to $R^{11}$ and $R^{12}$.

TIME represents a so-called timing group.

Typical examples include the group of the formula

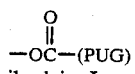

described in Japanese Patent Publication No. 9696/80 and Japanese Patent Application (OPI) Nos. 1139/83 and 1140/83 and the group of the formula $-OCH_2-(-PUG)$ described in Japanese Patent Application (OPI) No. 93442/84. The symbol n represents 0 or a positive integer, and preferably an integer of from 0 to 3.

PUG represents a photographically useful group.

The photographically useful groups (PUG) released from the precursor compounds are exemplified by antifoggants, development inhibitors, developing agents, development accelerators, electron donors (ED), fogging agents, nucleating agents, silver halide solvents, bleach accelerators, bleach-fix accelerators, fixation accelerators, dyes, color diffusion transfer reagents, couplers, melting point depressant agents for use in thermographic materials, and coupling inhibitors for use in the diazo photothermography.

Specific examples of antifoggants and development inhibitors include nitrogen-containing heterocyclic compounds having mercapto groups.

The developing agents and development inhibitors include, among others, hydroquinones, catechols, aminophenols, p-phenylenediamines, pyrazolidones, and ascorbic acid compound.

The electron donors, fogging agents and nucleating agents include, among others, α-hydroxyketones, α-sulfonamidoketones, hydrazines, hydrazides, tetrazolium salts, aldehydes, acetylenes, quaternary salts, and ylides.

The silver halide solvents are exemplified by thioethers, rhodanines, hypo (sodium thiosulfate), methylenebissulfones, and so on.

The bleach accelerators and bleach-fix accelerators include, among others, aminoethanethiols, sulfoethanethiols, aminoethanethiocarbamates, and so on. The fixation accelerators are typically represented by hypo.

The dyes include, for example, azo dyes, azomethine dyes, anthraquinone dyes, and indophenol dyes.

Among the above-mentioned photographically useful groups, those which have their effects manifested particularly well when blocked in the form represented by any of the formulae (I) to (III) are development inhibitors, and the development inhibitors which are especially beneficial in this respect are the groups represented by formula (IV).

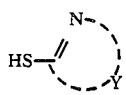 (IV)

wherein Y represents an atomic group necessary to complete a 5- or 6-membered heterocyclic ring (preferably containing sulfur, nitrogen, and/or oxygen atoms within the ring.) The blocking group is attached to the sulfur or nitrogen atom in formula (IV).

Among the groups represented by formula (IV), those having the following formulae are particularly desirable.

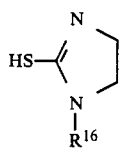

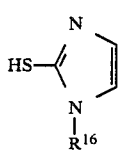

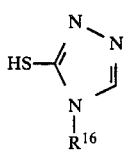

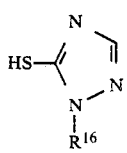

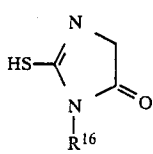

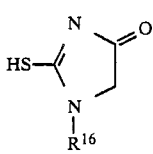

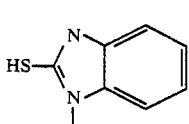

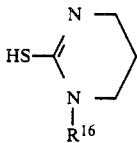

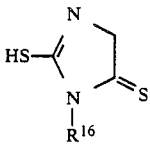

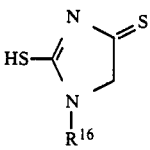

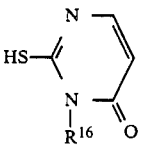

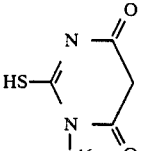

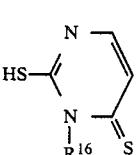

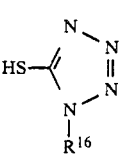

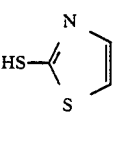

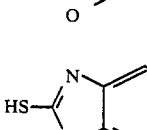

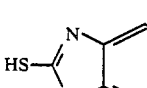

-continued

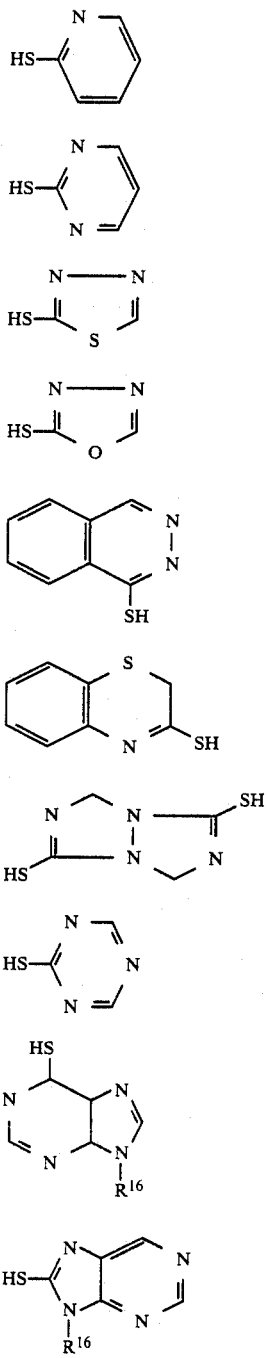

In the foregoing examples of formula (IV), $R^{16}$ represents a member selected from the group consisting of a hydrogen atom, an alkyl group, an aryl group, a cycloalky group, an alkenyl group and an aralkyl group, and these groups may have suitable substituents, such as the substituents described above for $R^{11}$. The carbon atoms constituting the above-given cyclic structures may have substituents other than hydrogen atoms, and typical examples of such substituents include those mentioned hereinbefore for $R^{11}$ and $R^{12}$.

Further, the compound obtainable by blocking a development inhibitor of the following formula (IV) in the form shown in any of formulae (I) to (III) is also useful.

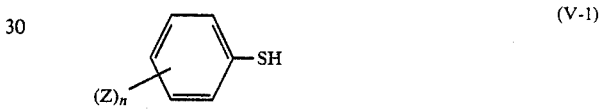

(wherein $R^{17}$ represents a substituted or unsubstituted alkyl group, a substituted or unsubstituted cycloalkyl group, a substituted or unsubstituted aralkyl group, a substituted or unsubstituted alkenyl group or a substituted or unsubstituted aryl group). The blocking group is attached to the sulfur atom in formula (V).

Examples of the substituent include, for example, an alkyl group, an aryl group, a cycloalkyl group, an aralkyl group, an alkoxy group, an aryloxy group, an alkylthio group, an arylthio group, an acyl group, an alkoxycarbonyl group, an amino group, a N-substituted amino group, an acylamino group, a carbamoyl group, a N-substituted carbamoyl group, an alkylsulfonyl group, an arylsulfonyl group, an alkylsulfonylamino group, an arylsulfonylamino group, a sulfamoyl group, a N-substituted sulfamoyl group, a cyano group and a nitro group, a halogen atom, and so on.

Among these substituents, preferred are an alkyl group, an alkoxy group, an aryloxy group, an alkoxycarbonyl group, an acylamino group and a sulfonylamino group and a halogen atom.

Among the compounds of formula (V), those having the following formula (V-1) are particularly beneficial.

$$\underset{(Z)_n}{\underset{\displaystyle\phantom{.}}{\text{[benzene ring]}}}\!-\!SH \qquad (V\text{-}1)$$

In the above formula (V-1), n represents an integer of 1 to 5; Z represents one of the substituents mentioned for $R^{17}$; provided that when n is equal to 2 or more, more than one occurrence of Z may be the same or different.

It should be understood that as the compound of formula (V) has an objectionable odor when its molecular weight is low, and has an increasingly greater antifoggant effect with an increased hydrophobicity of $R^{17}$, the number of carbon atoms is preferably at least 6, and, for better result, between 10 and 30, inclusive of substituents, if any.

It is known that mercapto group-containing compounds of formula (IV) or (V) exert a development inhibitory effect when used in a silver halide photosensitive material, and the use of such compounds in heat-developable photosensitive materials is also described, for example in Japanese Patent Application (OPI) No. 176351/84 and Japanese Patent Application (OPI) No. 111636/84.

However, when the compound of formula (IV) or (V) is directly incorporated in the emulsion layer, development is inhibited from the beginning so that the image density is decreased and the sensitivity is also reduced at times.

However, when the development inhibitor (IV) or (V) is blocked in the form of any of formulae (I) to (III), the development inhibitor (IV) or (V) is released gradually during the heat-development so that the development can be terminated without incurring decreases in image density.

Furthermore, by incorporating one of the compounds (I) to (III) according to the present invention, which is a blocked development inhibitor (IV) or (V), there can be obtained a heat-developable photosensitive material or dye fixing material having the property to complement a variation in heating temperature. As the development is carried out at a high temperature over 100° C., a minor temperature variation is usually unavoidable. And as the ultimate image density is high in the high temperature area and low in the low temperature area, as a whole an uneven image and, especially, an unevenness of fog density tends to be created. Moreover, development proceeds at times in the thermal transfer of the diffusible dye so that if the fog is increased or the heating temperature varies, the transferred image also becomes uneven.

However, when any of compounds (I) to (III) is incorporated, the development inhibitor (IV) or (V) is released in a relatively larger amount in the high temperature area and hence, the ultimate local image density is suppressed so that, as a whole, the unevenness of image density is mitigated.

The mechanism of action of the compounds (I) to (III) according to the present invention appears to be as follows. In the heat-development or transfer, the protective (blocking) group $R^1$ in the 1-position of the pyrazole ring is cleaved off under the influence of the nucleophilic agent to thereby form an anion (IV) (see the reaction scheme below) and the subsequent intramolecular transfer of lone pair electron leads to the release of PUG or a dissociated form thereof.

As an example, the decomposition scheme of the compound (III) is shown below.

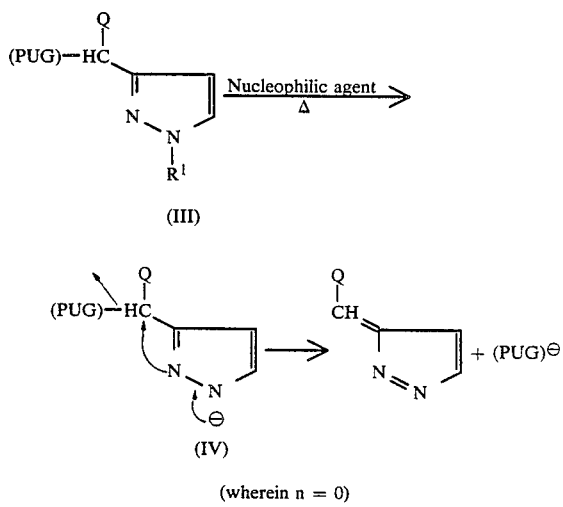

(wherein n = 0)

For the cleavage of the blocking group in the 1-position of the pyrazole ring, one must presuppose an attack by a nucleophilic reagent. Though the identity of this nucleophilic reagent is not clear, one may postulate the various terminal residues of amino acid moieties of gelatin, such as $-NH_2$, $-OH$, $-CO_{2l\,H}$, $-SH$,

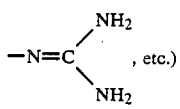

It was a surprising discovery that the reaction of the compound according to the present invention with said nucleophilic reagent as shown by the above scheme takes place effectively in a low water content layer during heating in a short space of time.

Moreover, when a base or a base precursor is used as the development accelerator in addition to any of the compounds (I) to (III), the base functions as a nucleophilic reagent during heating so as to promote release of PUG. For this reason, the combined use of a base or base precursor and any of the compounds (I) to (III) according to the present invention is particularly advantageous.

Preferred examples of the base or base precursor which can be used in combination with the compounds (I) to (III) according to the present invention are set forth below.

(a) Base

Preferred examples of the base include, among inorganic bases, the hydroxides, secondary or tertiary phosphates, borates, carbonates, quinolates and metaborates of alkali metals or alkaline earth metals, ammonium hydroxide, quaternary alkylammonium hydroxides, and other metal hydroxides, and, among organic bases, aliphatic amines (trialkylamines, hydroxylamines, aliphatic polyamines); aromatic amines (N-alkyl-substituted aromatic amines, N-hydroxyalkyl-substituted aromatic amines, bis[p-dialkylamino)phenyl]methanes, etc.), heterocyclic amines, amidines, cyclic amidines, guanidines, cyclic guanidines and so on. Particularly preferred are the based with a pKa value of 8 or more.

(b) Base precursor

The base precursor includes, among others, the salts of the bases with organic acids which are decomposed through decarboxylation upon heating, compounds which release amines on decomposition by such reactions as intramolecular nucleophilic displacement reaction, Lossen rearrangement, Beckmann rearrangement, etc., and compounds which undergo some reaction or other upon heating to release a base, to name some preferred examples. To be specific, preferred base precursors include the salts of trichloroacetic acid which are described in British Pat. No. 998,949, the salts of α-sulfonylacetic acid described in U.S. Pat. No. 4,060,420, the salts of propionilic acid described in Japanese Patent Application (OPI) No. 180573/84, the 2-carboxycarboxamide derivatives described in U.S. Pat. No. 4,088,496, the salts of heat-decomposable acids with organic bases or alkali or alkaline earth metals as described in Japanese Patent Application No. 69597/83, the hydroxamic acid carbamates utilizing Lossen rearrangement as described in Japanese Patent Application (OPI) No. 168440/84, and the aldoxime carbamates adapted to give rise to nitriles when heated as described in Japanese Patent Application (OPI) No. 157637/84, among others. Aside from the above, the base precursors described in British Pat. No. 998,945, U.S. Pat. No. 3,220,846, Japanese Patent Application (OPI) No. 22625/75 and British Pat. No. 2,079,480 are also useful.

The ratio of the base precursor to the compound according to the present invention is not limited but a preferred molar ratio of the base precursor to the compound (I) of the present invention, for instance, is from 1/20 to 20/1.

The following is an examplary listing of the compounds (I) through (III) according to the present invention. It should be understood, however, that the present invention is not limited to the use of these specific compounds.

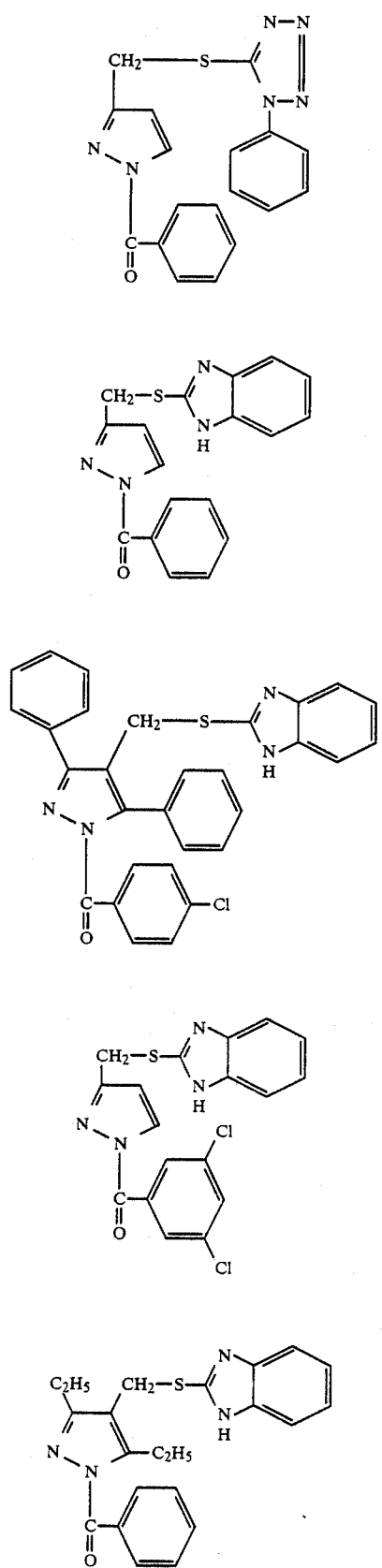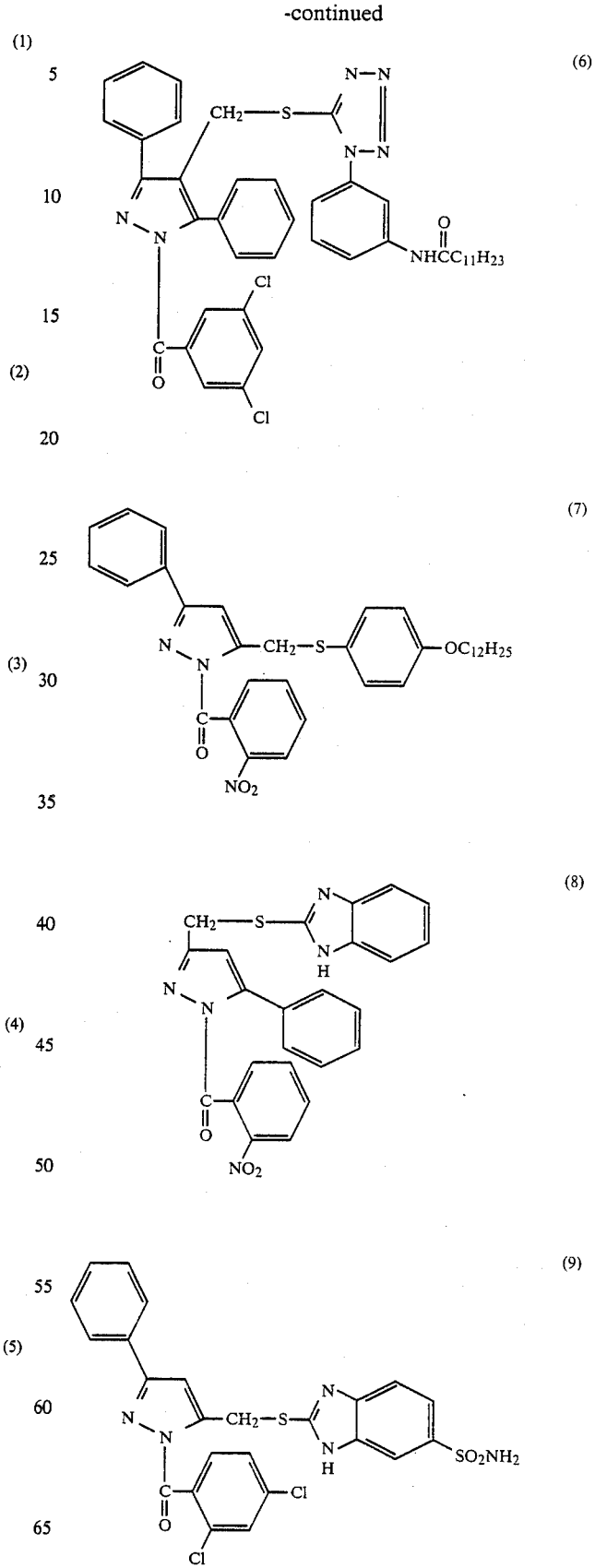

-continued
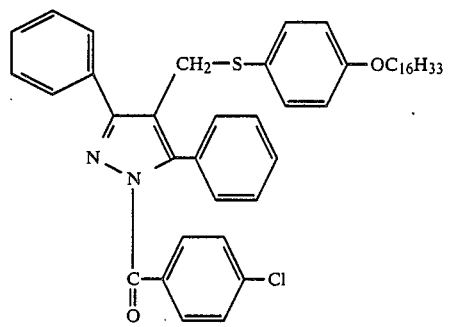
(10)
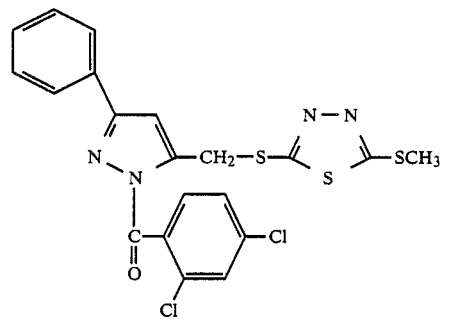
(11)
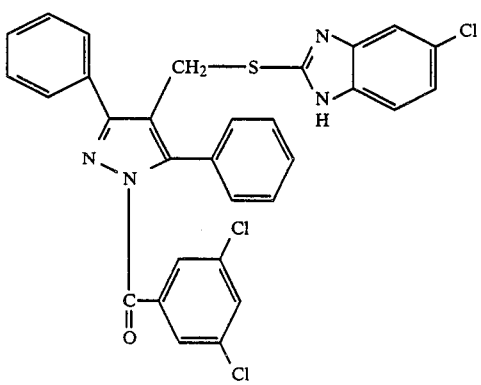
(12)
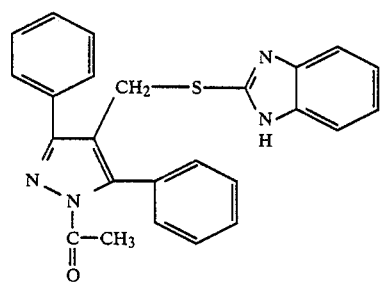
(13)
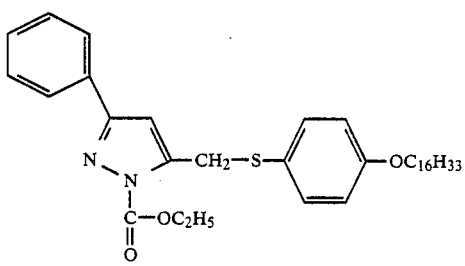
(14)
-continued
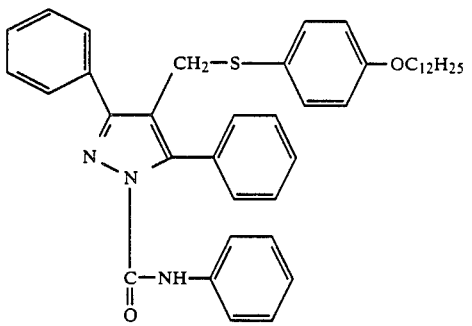
(15)
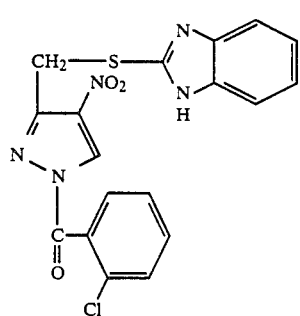
(16)
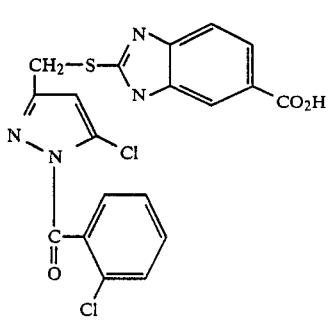
(17)
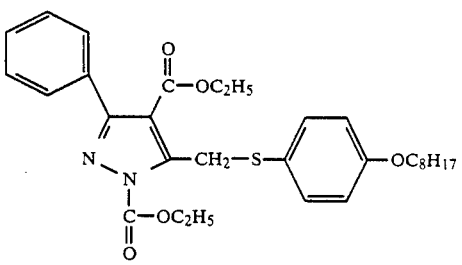
(18)
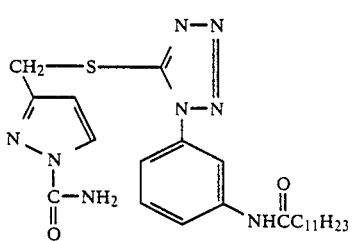
(19)

-continued
(17) 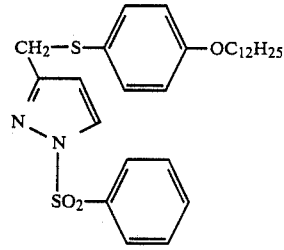
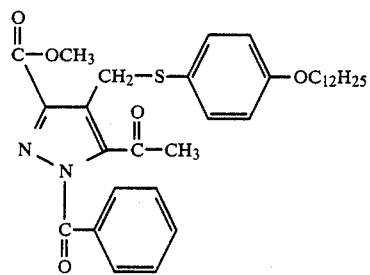
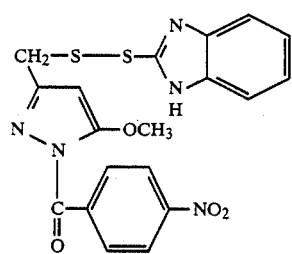
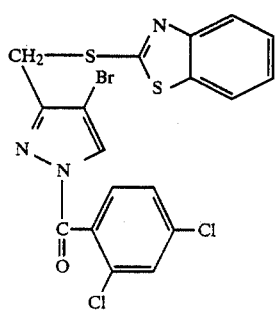
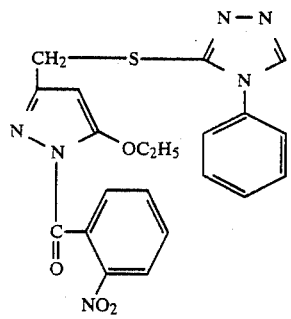
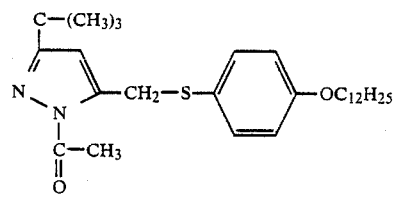
-continued
(20) 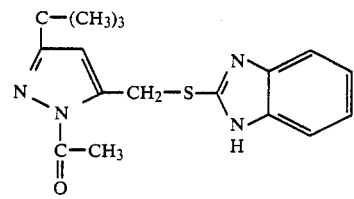
(21) 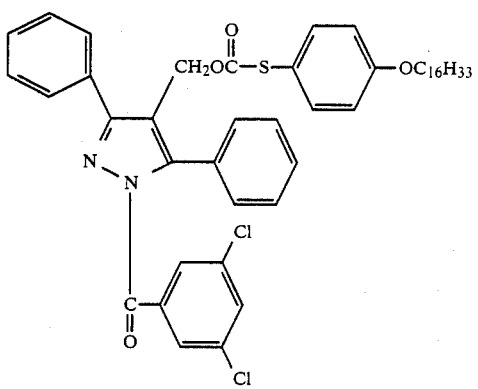
(22)
(23) 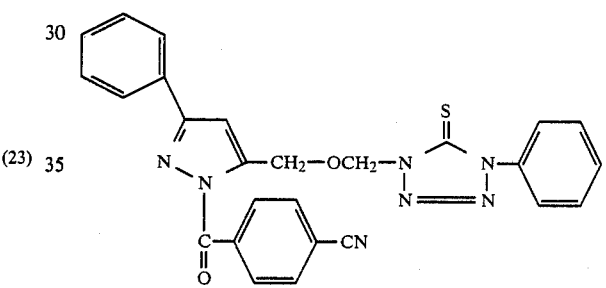
(24)
(25)
(26)
(27)
(28) 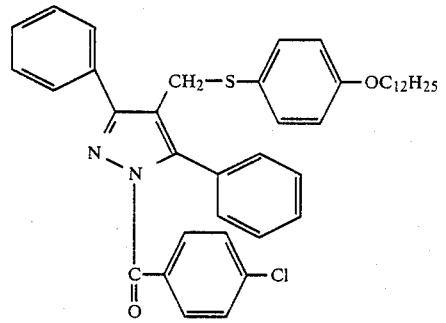
(29) 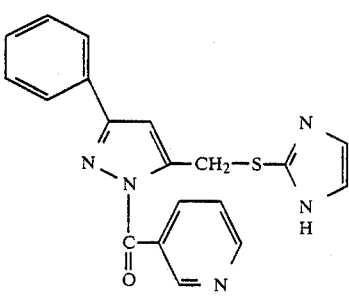
(30)

(31) 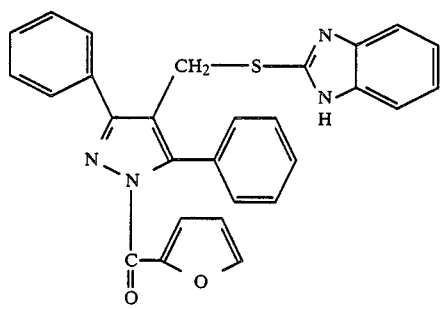
(36) 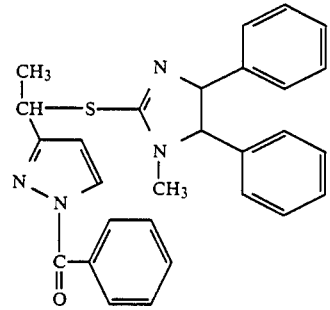
(32) 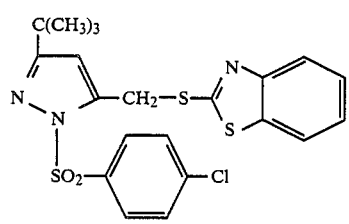
(37) 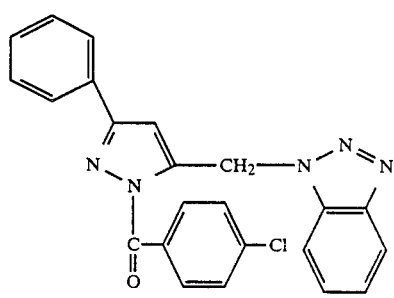
(33) 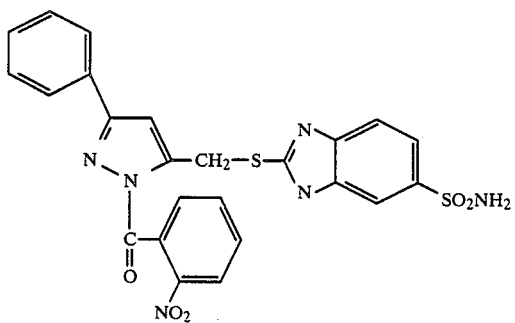
(38) 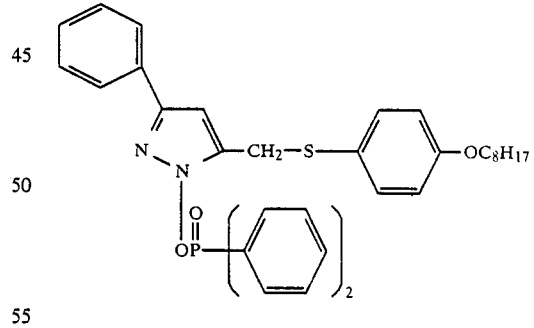
(34) 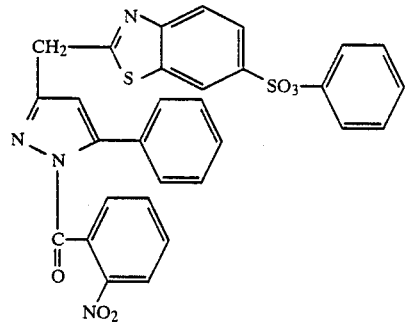
(39) 
(35) 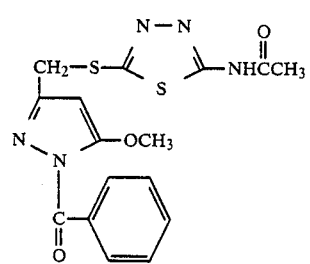
(40) 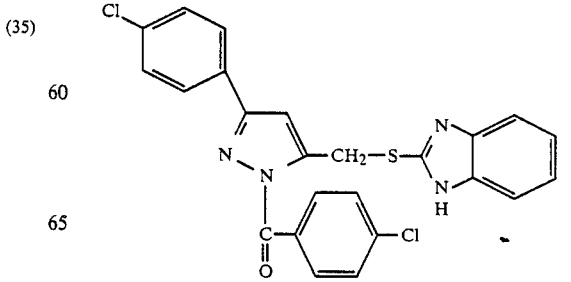

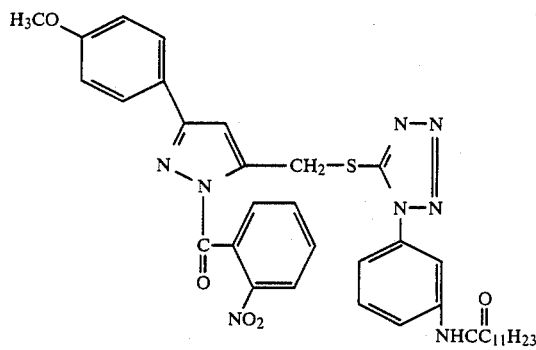
(41)

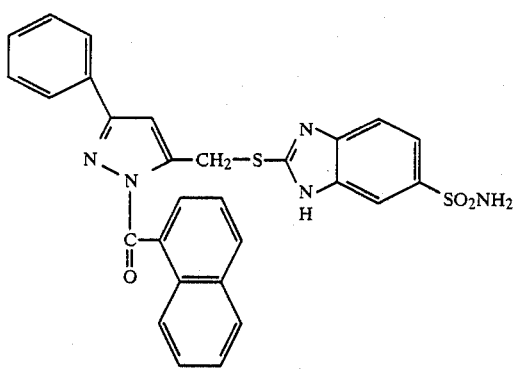
(42)

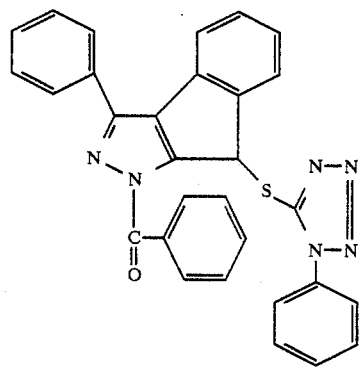
(43)

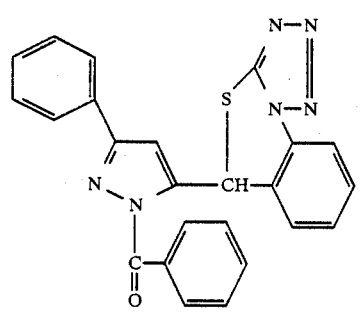
(44)

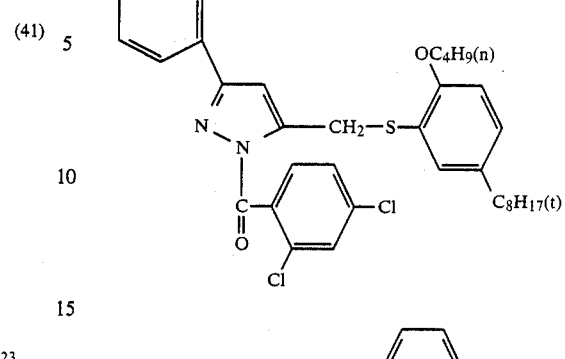
(45)

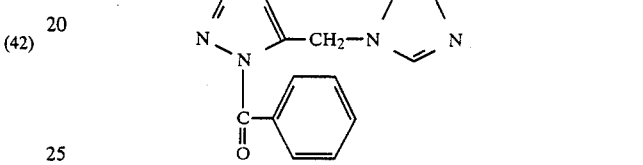
(46)

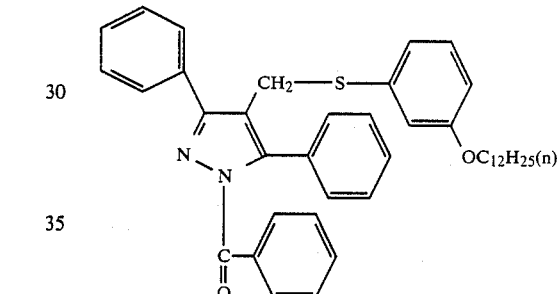
(47)

The method for synthesizing the compounds of the present invention is described below.

The compound (Q=H) according to the present invention can be synthesized using a methyl-substituted pyrazole (VII) as the starting compound.

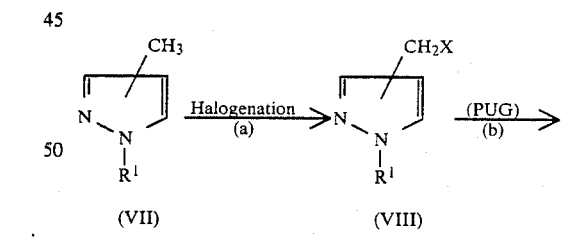

In the foregoing, (wherein X represents halogen atom).

A general method for production of (VII) is described, for instance, in L. C. Behr et al: *Pyrazoles, Pyrazolines, Pyrazolidines, Indazoles and Condensed Rings*, pp. 137–140, Interscience, 1967.

The halogenation of the side chain in step (a) is conducted using a chlorine atom, sulfuryl chloride, a bromine atom, N-chlorosuccinimide, N-bromosuccinimide or the like. This reaction is preferably carried out with the aid of a radical initiator such as benzoyl peroxide (BPO), azobisisobutyronitrile (AIBN) or the like. Frequently, irradiation with light is also effective.

The substitution reaction in step (b) is preferably conducted using an inorganic base such as triethylamine or an inorganic base such as potassium carbonate. When (PUG) is a compound represented by (IV) or (V), it is advantageous to prepare the sodium salt of the thiol, for the reaction then proceeds smoothly.

Specific examples of synthesis are set forth below.

Synthesis of Compound (7)

Synthesis of 1-(o-nitrobenzoyl)-3-phenyl-5-methylpyrazole

This compound was synthesized from o-nitrobenzoylhydrazine and benzoylacetone in accordance with the method described in *J. Prakt. Chem.*, Vol. 139, p. 65 (1934).

Synthesis of Compound (7)

A carbon tetrachloride solution (300 ml) containing 30.7 g (0.1 mole) of the above compound, 17.8 g (0.1 mole) of N-bromosuccinimide and 0.3 of benzoyl peroxide was refluxed under light irradiation for 5 hours. The reaction mixture was then cooled to room temperature and the precipitated succinimide was filtered off. The filtrate was distilled under reduced pressure and the residue was subjected to thin layer chromatography and NMR spectrometry for identification. By these analyses, the product was confirmed to be a mixture 5-methyl, 5-bromomethyl and 5-dibromomethyl compounds, with the bromomethyl compound accounting for about 70 percent.

To the above mixture were added 10.5 g (0.7 mole) of 2-mercaptobenzimidazole, 9.7 g (0.07 mole) of anhydrous potassium carbonate and 300 ml of acetone, and the whole mixture was refluxed while stirring for 2 hours.

The inorganic salt was then filtered off and the filtrate was concentrated. The concentration residue was purified by silica gel column chromatography to provide 18.0 g of Compound (7).

Yield 57% (based on 2-mercaptobenzimidazole)

m.p. 92°–95° C.

While the amount of the compound according to the present invention varies with each individual compound and the system in which it is used, it is generally up to 50 weight percent on the basis of the weight of the coat and preferably up to 30 weight percent on the same basis. The optimum amount is largely dependent on the structure of the development inhibitor (IV) or (V) that is released. Further, some of the development inhibitors (IV) and (V) are such that they accelerate development when used in small amounts, but inhibit development when used in increased amounts. Therefore, the addition of the compounds (I) to (III) which release such compounds (IV) or (V) is especially advantageous, for development is then accelerated in an early phase and inhibited in a later phase.

The compound according to the present invention can be dissolved first in a water-soluble organic solvent (for example, methanol, ethanol, acetone, dimethylformamide, etc.) or a mixture of such organic solvent and water, and then incorporated in the binder.

The hydrophobic compound according to the present invention can be incorporated in microfine particles in the binder by the technique described in Japanese Patent Application (OPI) No. 174830/84. While this patent literature describes a method for dispersing a base precursor in an ultrafine particulate form in the binder, the method is suitable for dispersing not only the hydrophobic compound according to the present invention, but also other hydrophobic (particularly those sparingly soluble in organic solvents) additives such as acid precursors, antifoggant precursors, etc., stably in a hydrophilic binder.

The compounds according to the present invention can be used singly or in combination. Furthermore, they may be used in combination with other kinds of development inhibitors or in conjunction with other development restraining techniques. Known development inhibitors and development terminating techniques include a method utilizing heat decomposition of an aldoxime ester as described in Japanese Patent Application Nos. 216928/83 and 48305/84, a method utilizing a Lossen rearrangement reaction as described in Japanese Patent Application No. 85834/84, and a method utilizing a carboxylic acid ester as described in Japanese Patent Application No. 85836/84 among others.

The terminology "image forming method including a heating step" is used herein to mean any photothermographic or thermographic process that includes a heating step in any of the image-forming steps, irrespective of whether the heating is done for development or for transfer of an image.

The heat-developable photosensitive material used in the image forming process involving a heating step for development includes one using silver halide or one using a diazo compound. The compound according to the present invention may be incorporated in such a photosensitive material, or, when an image receiving layer is provided on a separate support, may be incorporated in an optional layer or layers on that support. The compound according to the present invention may also be supplied from an external source in the heating step.

In practicing the image forming method including a heating step in accordance with the present invention, it is preferable to employ what is known to be a heat-developable photosensitive material, inclusive of those described in the prior art literature referred to hereinbefore. Thus, compounds of formulae (I) to (III) can be incorporated in any of the layers existing on the support (for example, the light-sensitive layer, intermediate layer, protective layer) or in a material (dye fixing element) used for fixation of an imagewise distributed mobile dye.

The most desirable heat-developable photosensitive material is one employing silver halide as a photosensitive substance.

An appropriate heating temperature is generally from about 50° C. to about 250° C., and a particularly useful temperature range is from 60° C. to 180° C.

The silver halide that can be used in the practice of the present invention can be produced, for example by the method described in U.S. Pat. No. 4,500,626 and may include the additives mentioned there, and the silver halides having the characteristics described there can be employed.

The silver halide emulsion may be used without ripening, but is generally subjected to chemical sensitization. The ordinary emulsions for photosensitive materials may be sensitized by sulfur sensitization, reduction sensitization and/or noble metal sensitization for use in the practice of the present invention.

The silver halide emulsion used in accordance with the present invention may be of the surface latent image type wherein a latent image is predominantly formed on the grain surface, or of the internal latent image type wherein a latent image is predominantly formed in the interior region of the grain. It is also possible to employ a direct reversal emulsion made up of an internal latent image emulsion and a nucleating agent.

The coverage of photosensitive silver halide in the practice of the present invention may range from 1 mg to 10 g, as silver, per square meter.

In the present invention, an organic metal salt, particularly an organic silver salt, which is comparatively resistant to light, is preferably used as an oxidizing agent in combination with photosensitive silver halide.

A detailed description of the organic silver salts that can be used is given in U.S. Pat. No. 4,500,626.

The silver halide that is employed in the practice of the present invention may be spectrally sensitized with a methine dye or the like.

For detailed information on such dyes, reference may be made to U.S. Pat. No. 4,500,626.

In the present invention, a reducing agent is incorporated in the photosensitive material. As the reducing agent, the reducing dye donors described hereinafter, as well as the reducing agents known in the art, are preferred.

As the reducing agents that can be employed in the present invention, those described in U.S. Pat. No. 4,500,626 may be mentioned, by way of example.

In the present invention, there can be incorporated a dye donor compound adapted to form or release a mobile dye in accordance or in reverse accordance with the reduction of photosensitive silver halide to silver at elevated temperature.

The dye donor compound is described below.

As examples of the dye donor compounds that can be used in the present invention, couplers capable of reacting with the developing agent may first be mentioned. The technique of utilizing this type of coupler is such that the developing agent oxidized by redox-reaction with the silver salt reacts with the coupler to form a dye, and has been described in many publications. Specific examples of the developing agents and couplers are described in detail, for example in T. H. James: *The Theory of the Photographic Process*, 4th Edition, Macmillan Publishing Co., 1977, pages 291–334 and pages 354–361, and Shinichi Kikuchi: *Shashin Kagaku*, 4th Edition (Kyoritsu Shuppan), pages 284–295, among others.

The dye-silver compound, consisting of an organic silver salt and a dye, may also be mentioned as an example of said dye donor compound.

Examples of such dye-silver compound are set forth in *Research Disclosure* pages 54–58 (RD-16966) (May, 1978), among other.

The azo dye that is used in the heat-development silver dye bleaching method can also be mentioned as an example of said dye donor compound. Specific examples of such azo dyes and the bleaching technique are described in U.S. Pat. No. 4,235,957 and *Research Disclosure* pages 30–32 (RD-14433) (April, 1976), among others.

The leuco dyes described in U.S. Pat. Nos. 3,985,565 and 4,022,617, for instance, can also be counted among the dye donor compounds.

A further example of the dye donor compound include a compound adapted to imagewise release or spread a diffusible dye. Compounds of such type can be represented by formula [L₁]

$$(Dye-X)_n-Y \qquad [L_1]$$

wherein Dye represents a dye group or a dye precursor group; X represents a chemical bond or a divalent linking group; and Y represents a group which either causes an imagewise differential in the diffusibility of the compound (Dye-X)n-Y in correspondence or reverse correspondence with the photosensitive silver salt carrying a latent image or releases the Dye and causes a differential in diffusibility between the released Dye and (Dye-X)n-Y; n represents 1 or 2 and when n is equal to 2, the two Dye-X groups may be the same or different.

The dye donor compound of general formula [L1] is exemplified by the dye developer consisting of a hydroquinone type developer component and a dye component which is described in U.S. Pat. Nos. 3,134,764, 3,362,819, 3,597,200, 3,544,545 and 3,482,972, for instance. The compounds which release diffusible dyes through intermolecular nucleophilic substitution reaction are described in Japanese Patent Application (OPI) No. 63618/76, among others, and the compounds which release diffusible dyes through a manner of winding inside the molecule of isooxazolones are described in Japanese Patent Application (OPI) No. 111628/74, for instance.

These systems are invariably such that a diffusible dye is released or spread in undeveloped areas and not released or spread in developed areas.

As an alternative system, there has been developed a system in which a dye releasing compound is made into an oxidized form which has no dye-releasing property and allowed to be present concomitantly with a reducing agent or a precursor thereof, and after development, is reduced by the residual unoxidized reducing agent so as to release a diffusible dye. Specific examples of the dye donor compounds used in this system are set forth in Japanese Patent Application (OPI) Nos. 110827/78, 130927/79, 164342/81, and 35533/78 among others.

On the other hand, as the substance which releases a diffusible dye in the developed area, the substance which releases a diffusible dye through reaction of a coupler moiety having the diffusible dye as a cleavage group with an oxidized developing agent is described in Bristish Pat. No. 1,330,524, Japanese Patent Publication No. 39165/73 and U.S. Pat. No. 3,443,940, among others, and the substance adapted to form a diffusible dye through reaction of a coupler moiety having a non-diffusing group as a cleavage group with an oxidized developing agent has been described, for example in U.S. Pat. No. 3,227,550.

Moreover, in these systems employing such color developers, the image spoilage by the oxidation products of a developing agent presents a serious problem, and, to obtain improvements in this respect, there have been developed dye donor compounds which does not require a developing agent, but rather have a reducing property per se.

Typical examples of such dye donor compounds are given in the literature noted below.

The definitions in the respective formulae can be found in the corresponding literature. The various dye donor compounds described, for example, in U.S. Pat. Nos. 3,928,312, 4,053,312, 4,005,428 and 4,336,322, Japanese Patent Application (OPI) Nos. 65832/84, 69839/84, 3819/78 and 104343/76, Research Disclosure 17465, U.S. Pat. Nos. 3,725,062, 3,728,113, and 3,443,939, and Japanese Patent Application (OPI) No. 116537/83 can all be employed in the practice of the present invention.

Specific examples of the dye donor compound that can be employed in the present invention are set forth in Japanese Patent Application (OPI) 84236/84 noted above.

The dye donor compounds and photographic additives that are employed in accordance with the present invention can be incorporated into layers of the photosensitive material by the known procedures including the method described in U.S. Pat. No. 2,322,027. In such procedures, the high-boiling organic solvents and low-boiling organic solvents referred to hereinbefore can be employed.

Moreover, dispersing methods using polymers as described in Japanese Patent Publication No. 39853/76 and Japanese Patent Application (OPI) No. 59943/76 can be utilized. Further, various surfactants can be used in dispersing the dye donor compound into a hydrophilic colloid.

In the practice of the present invention, an image formation accelerator can be used in the photosensitive material. The image formation accelerators include those which promote the redox reaction between the silver salt oxidizing agent and the reducing agent, those which promote formation of a dye from a dye donor substance or decomposition of a dye, and those which promote various reactions such as the release of a mobile dye, and those which accelerate the migration of a dye from a photosensitive layer to a dye fixing layer. Classified by physicochemical function, the image formation accelerators can be classified into the above-mentioned bases or base precursors, nucleophilic compounds, oils, thermal solvents, surface active agents, and compounds which interact with silver or silver ions, for instance. However, each of these substances generally has plural functions and provides several of the above-mentioned effects.

A detailed discussion on these substances and their functions can be found in U.S. Pat. No. 4,500,626.

In the practicing the present invention, various development terminating agents can be used in the photosensitive material for the purpose of ensuring a constant image quality irrespective of variations in the thermal development temperature or processing time.

The terminology "development terminating agent" as used herein means a compound which, after proper development, quickly neutralizes the base or reacts with the base to lower the base concentration in the layer and thereby terminates the development or a compound which interacts with silver and silver salt to arrest development.

Further, in carrying the present invention into practice, a compound which activates development, and, at the same time, serves to stabilize the image, can be incorporated in the photosensitive material.

In the practice of the present invention, an image toner can be incorporated in the photosensitive material. Useful examples of the toners are mentioned in U.S. Pat. No. 4,500,626.

The binder used in the photosensitive material according to the present invention may be a single binder or a combination of two or more binders. Hydrophilic binders can be utilized and typical examples of such binders are transparent or translucent binders. More specifically, natural substances such as proteins, e.g. gelatin, gelatin derivatives, etc., and polysaccharides, e.g., cellulose derivatives, starch, gum arabic, etc., and synthetic polymers such as water-soluble polyvinyl compounds, e.g., polyvinyl pyrrolidone, polyacrylamide, and so on. Among other synthetic polymers that can be used are dispersible vinyl compounds in latex form which contribute to the dimensional stability of photographic materials.

In accordance with the present invention, the binder is used in a coverage of 20 g or less per square meter, preferably in a coverage not exceeding 10 g per m$^2$, and, for still better results, not more than 7 g/m$^2$.

The proportion of the high-boiling organic solvent which is dispersed together with the hydrophobic compound such as said dye donor compound in the binder is not more than 1 cc to each gram of the binder, preferably not more than 0.5 cc per gram of the binder, and for still better results, not more than 0.3 cc on the same basis.

In the photographic light-sensitive element and dye-fixing element in accordance with the present invention, either an inorganic hardener or an organic hardener can be incorporated in the photographic emulsion layer and/or other binder layer.

Specific examples of the procedure and of the compounds are set forth in U.S. Pat. No. 4,500,626 and these compounds can be used singly or in combination.

The support which is used in the light-sensitive element, and, depending on the intended application, in the dye-fixing element as well, may be any support that withstands the processing temperature. As the support materials, glass, paper, metal and other analogous materials can be employed and those mentioned as support materials in U.S. Pat. No. 4,500,626 can also be utilized.

When the dye donor used in accordance with the present invention is a donor compound adapted to imagewise release a mobile dye, a dye migration assisting agent may be used for assisting in the transfer of the dye from the light-sensitive layer to the dye fixing layer.

In a system where a dye migration assisting reagent is supplied from an external source, water or a basic aqueous solution containing sodium hydroxide, potassium hydroxide, an inorganic metal salt or an organic base can be used as the dye migration assisting agent. The base may be those mentioned in connection with the image formation accelerator. Moreover, a low-boiling solvent such as methanol, N,N-dimethylformamide, acetone, diisobutyl ketone, etc., or a mixture of such a low-boiling solvent with water or a basic aqueous solution can be employed. The dye migration assisting agent may be used in such a manner that it wets either the dye fixing element or the light-sensitive element or both.

When a colored dye-donor compound is contained in the light-sensitive element used in the practice of the present invention, it is not so necessary to incorporate an anti-irradiation or anti-halation agent and/or other dyes in the light-sensitive element but the filter dyes and absorbent substances can be incorporated.

The light-sensitive element employed in the present invention may contain, if desired, various additives known in the art of photothermography and also include various layers other than light-sensitive layers, such as the antistatic layer, conductive layer, protective layer, intermediate layer, anti-halation layer, separating layer and so on which are known in the art. Examples of additives include the additives described in Research Disclosure 170, No. 17029 (June, 1978), such as plasticizers, sharpness improving dyes, anti-halation (AH) dyes, sensitizing dyes, matting agents, surface active agents, fluorescent whiteners, anti-fading agents, and so on, may be mentioned.

The photographic material according to the present invention comprises a light-sensitive material adapted to form or release a dye upon heat-development, or, if desired, consists of such a light-sensitive element and a dye fixing element.

Particularly, in a system where an image is formed by the diffusion transfer of a dye, both of such light-sensitive and dye-fixing elements are necessary, and the system may be classified into two major categories, a format in which the light-sensitive element and the dye-fixing element are respectively disposed on two independent supports and a format in which the two elements are provided as coating layers on one and same support.

As regards the relation between the dye element and dye-fixing element, the relation thereof with the support and the relation thereof to the white reflective layer, those described in U.S. Pat. No. 4,500,626 are applicable to the present invention.

Representative of the format in which the light-sensitive element and dye-fixing element are coated on the same support is the format in which the light-sensitive element need not be separated from the image receiving element after formation of the transferred image. In this system, the light-sensitive layer, dye fixing layer and white reflective layer are disposed in superimposition on a transparent or opaque support. A preferred example of this format is described in U.S. Pat. No. 4,500,626.

Another representative format in which the light-sensitive element and dye fixing element are disposed on the same support is the format which is so designed as to peel apart or all of the light-sensitive element from the dye-fixing element, as described in Japanese Patent Application (OPI) No. 67840/81, Canadian Pat. No. 674,082 and U.S. Pat. No. 3,730,718, for instance.

The light-sensitive element or the dye fixing element may comprise a conductive heat element-containing layer as means for heat-development or diffusion transfer of the dye.

The light-sensitive element used in accordance with the present invention for the purpose of obtaining a broad range of color within the color chart using the three color primaries of yellow, magenta and cyan must have at least three silver halide emulsion layers having different spectral sensitivities.

Representative combinations of at least 3 silver halide emulsion layers having different spectral sensitivities are described in U.S. Pat. No. 4,500,626.

The light-sensitive element used in the practice of the present invention may comprise, as required, two or more distinct emulsion layers of the same spectral sensitivities but of different speeds.

The above-mentioned emulsion layers and/or the non-sensitive hydrophilic colloid layers adjacent thereto must contain at least a species of the substances described in U.S. Pat. No. 4,500,626.

The light-sensitive element used in accordance with the present invention may have, in addition to the above layers, various auxiliary layers as necessary, said auxiliary layers such as a protective layer, a intermediate layer, an antistatic layer, an anti-curling layer, a peel-apart layer, a matting layer and the like.

Particularly, in the protective layer, it is common practice to incorporate an organic or inorganic matting agent for prevention of adhesion. Further, a mordant, a ultraviolet absorber and the like may also be incorporated in this protective layer. The protective layer and intermediate layer may each consist of two or more units.

In the intermediate layer, a reducing agent may be incorporated for preventing mixing of colors, a UV absorber, a white pigment such as $TiO_2$, and so on. The white pigment may be added not only to the intermediate layer but also to the emulsion layers for increased sensitivity.

The dye fixing element used in accordance with the present invention has at least one layer containing a mordant, and in a format in which the dye fixing layer is disposed on the surface, a further protective layer may be provided if necessary.

With regard to the layer construction, binder, additives and the method of addition and the position of the mordant in the dye fixing element, those described in U.S. Pat. No. 4,500,626 are applicable to the present invention.

The dye fixing element used in the practice of the present invention may have separating, matting, anti-curling, and other auxiliary layers, if desired, in addition to the above-mentioned layers.

In one or more layers among the above-mentioned layers, there may also be incorporated a base and/or a base precursor for promoting migration of the dye, a hydrophilic thermal solvent, an anti-fading agent for preventing mixing of colors, a UV absorber, a vinyl compound dispersion for increasing the dimensional stability, a fluorescent whitener, and so on.

The binder to be used in the above-mentioned layers is preferably a hydrophilic binder, which is exemplified by transparent and translucent hydrophilic colloids. To be specific, the binders mentioned hereinbefore in connection with the light-sensivtive element may be employed.

Further, in its preferred mode, the dye fixing element according to the present invention contains an auxiliary image transfer agent which is described hereinafter. The auxiliary image transfer agent may be incorporated in the dye fixing layer itself or in an independent layer.

In a system of the present invention wherein electric heating is employed as a development means, the transparent or opaque heating element can be prepared by known techniques for the production of a resistance heating element.

As the resistance heating element, there is a system employing a thin film of semi-conductive inorganic material or a system utilizing a thin film comprising a dispersion of conductive fine powders in an organic binder. As to the materials that can be used in such systems, those described in U.S. Pat. No. 4,500,626 can be utilized.

Regarding the image receiving layer according to the present invention, it may be a dye fixing layer used in a heat-developable color photosensitive material, and while a choice may be made from among the mordants commonly used, polymeric mordants are particularly preferred. The term "polymeric mordant" is used herein to mean any of tertiary amino group-containing polymers, nitrogen-containing heterocyclic ring-containing polymers and the corresponding quaternary cation group-containing polymers, for instance.

In accordance with the present invention, the coating methods for various layers such as a heat-developable light-sensitive layer, a protective layer, an intermediate layer, a subbing layer, a backing layer, etc. can be as those described in U.S. Pat. No. 4,500,626.

As the light source for imagewise exposure for recording an image on the thermally developable light-sensitive element, various radiations including light in the visible region, can be employed, and, for example, the sources of light described in U.S. Pat. No. 4,500,626 can be utilized.

Regarding the heating temperature used in the heat-development process, the development can be effected at a temperature between about 80° C. to about 250° C. and the particularly useful temperature range is from about 110° C. to about 180° C. The heating temperature in the transfer process may range from the development temperature to room temperature but it is preferable to use a higher temperature, up to about 10° C. below the heat-development temperature. As the heating means for use in the development process and/or the transfer process, use may be made of various means such as a hot plate, an iron, a thermal roller, a heating element utilizing carbon or titanium white, and so on.

Further, as described in detail in Japanese Patent Application No. 218443/84, the method in which development and transfer are carried out either at the same time or in a continuous sequence can be advantageously utilized. In this method, said image formation promoting agent and/or dye migration assisting agent may be previously incorporated in either one or both of the dye fixing element and light-sensitive element or supplied from the outside. In this system where development and transfer are carried out simultaneously or in a continuous sequence, the heating temperature is preferably more than 60° C. and less than the boiling point of the solvent used for the transfer process. For example, when the transfer solvent is water, a temperature between 60° C. and 100° C. is preferred.

The dye migration assisting agent (for example, water) is generally spread between the light-sensitive layer of the heat-developable light-sensitive element and the dye fixing layer of the dye fixing element to thereby accelerate the transfer of the image but it is possible to previously apply the dye migration assisting agent to either the light-sensitive layer or the dye fixing layer or to both, and then laminate the two layers.

Methods for applying the dye migration assisting agent to the light-sensitive layer or the dye fixing layer are described, for example, in U.S. Pat. No. 4,500,626.

The heating means that can be used in the transfer process are described in U.S. Pat. No. 4,500,626. As an alternative, one may superimpose a conductive layer of graphite, carbon black, or metal on the dye fixing material and pass an electric current through the conductive layer so as to directly heat the system.

The heating temperature for use in this transfer process may range from the temperature used in the development process to room temperature, but preferably more than 60° C. and less than about 10° C. below the heat development temperature.

The pressure conditions and methods for applying the pressure that can be used in laminating the heat-developable light-sensitive element to the dye fixing element are described in U.S. Pat. No. 4,500,626.

As the heating step in the present invention is carried out in the presence of at least one member selected from the group consisting of compounds of formulae (I), (II) and (III), the image forming method according to the present invention provides for little variation in photographic characteristics even when a variation in heating temperature occurs.

This is because the above compound is stable at room temperature and has the function to release the photographically useful group for the first time at the heat-development stage and/or heat-transfer stage.

The following examples illustrate the present invention in further detail, but are not to be construed as limiting the scope of the invention.

EXAMPLE 1

The procedure for preparation of a silver iodobromide emulsion is described below.

In 3,000 ml of water were dissolved 40 g of gelatin and 26 g of KBr. This solution was stirred at a constant temperature of 50° C.

Then, a solution of 34 g of silver nitrate in 200 ml of water was added to the above solution over a period of 10 minutes.

Thereafter, a solution of 3.3 g of KI in 100 ml of water was added to the above mixture over 2 minutes.

The pH of the resulting silver iodobromide emulsion was adjusted for precipitation and the excess salt was removed.

Then, the emulsion was adjusted to a pH of 6.0, whereby a silver iodobromide emulsion was obtained in a yield of 400 g.

The procedure for preparation of a gelatin dispersion of a dye donor compound is described below.

Five grams of Yellow Dye Donor Compound (1) and, as a surface active agent, 0.5 g of 2-ethylhexyl sodium sulfosuccinate and 10 g of tri-iso-nonyl phosphate were weighed out, and 30 ml of ethyl acetate was added. The mixture was heated at about 60° C. to obtain a homogeneous solution. This solution was mixed with 100 g of a 10% solution of lime-treated gelatin under stirring and the mixture was homogenized in a homogenizer at 10,000 rpm for 10 minutes. This dispersion is designated as a yellow dye donor dispersion.

In the same manner as above except that Magenta Dye Donor Compound (2) was used, a magenta dye donor dispersion was prepared. Similarly, a cyan donor dispersion containing Cyan Dye Donor Compound (3) was also prepared.

Dye donor compound

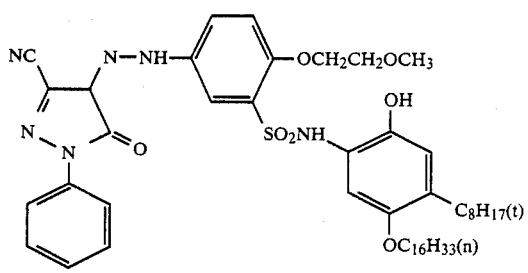
(1)

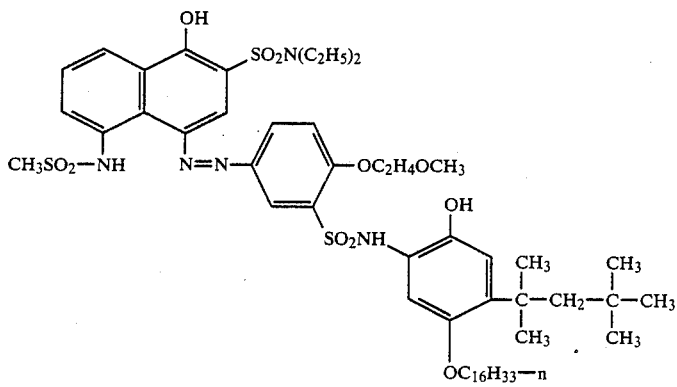
(2)

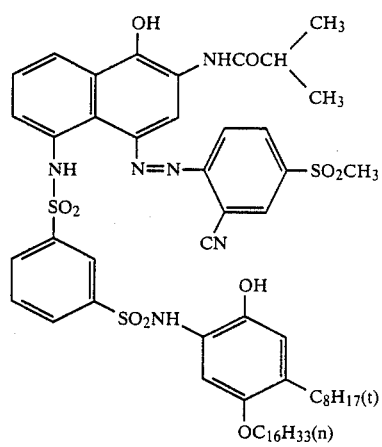
(3)

The procedure for preparation of a gelatin dispersion of the compound according to the present invention is described below.

To 100 g of a 1% aqueous solution of gelatin was added 3 g of Compound (3) according to the present invention and the mixture was ball-milled for 10 minutes using 100 g of glass beads with a mean diameter of about 0.6 mm. The glass beads were filtered off to recover a gelatin dispersion of the compound according to the present invention.

Then, on a support a multi-layer color light-sensitive material A was prepared as described below.

The sixth layer: Layer containing 1,000 mg/m$^2$ of gelatin, 220 mg/m$^2$ of a base precursor*$^3$, 10 mg/m$^2$ of Compound (3) of the invention.

The fifth layer: Blue-sensitive emulsion layer containing a silver iodobromide emulsion (containing 10 mol% of iodine and 400 mg/m$^2$ of silver), 180 mg/m$^2$ of benzenesulfonamide*$^4$, 520 mg/m$^2$ of a base precursor*$^3$, 5 mg/m$^2$ of Compound (3) of the invention, 400 mg/m$^2$ of Yellow Dye Donor (1), 1,000 mg/m$^2$ of gelatin, 800 mg/m$^2$ of high boiling point solvent*$^1$, and 100 mg/m$^2$ of a surfactant*$^2$.

The fourth layer: Intermediate layer containing 1,200 mg/m$^2$ of gelatin, 200 mg/m$^2$ of a base precursor*$^3$, and 10 mg/m$^2$ of Compound (3) of the invention.

The third layer: Green-sensitive emulsion layer containing a silver iodobromide emulsion (containing 10 mol% of iodine and 400 mg/m$^2$ of silver), 180 mg/m$^2$ of benzenesulfonamide*$^4$, 10$^{-6}$ mol/m$^2$ of Sensitizing Dye (D-I), 515 mg/m$^2$ of a base precursor*$^3$, 5 mg/m$^2$ of Compound (3) of the invention, 400 mg/m$^2$ of Magenta Dye Donor (2), 1,000 mg/m$^2$ of gelatin, 800 mg/m$^2$ of a high boiling point solvent*$^1$, and 100 mg/m$^2$ of a surfactant*$^2$.

The second layer: Intermediate layer containing 1,000 mg/m$^2$ of gelatin, 230 mg/m$^2$ of a base precursor*$^3$, and 10 mg/m$^2$ of Compound (3) of the invention.

The first layer: Red-sensitive emulsion layer containing a silver iodobromide emulsion (containing 10 mol% of iodine and 400 mg/m$^2$ of silver), 180 mg/m$^2$ of benzenesulfonamide*$^4$, 8×10$^{-7}$ mol/m$^2$ of Sensitizing Dye (D-2), 515 mg/m$^2$ of a base precursor*$^3$, 5 mg/m$^2$ of Compound (3) of the invention, 300 mg/m$^2$ of Cyan Dye Donor (3), 1,000 mg/m$^2$ of gelatin, 600 mg/m$^2$ of a high boiling point solvent*$^1$, and 100 mg/m$^2$ of a surfactant*$^2$.

Ingredients employed therein are illustrated below.

(iso C$_9$H$_{19}$O)$_3$P=O    *1

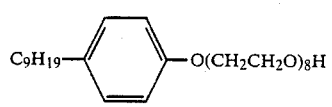 *2

-continued

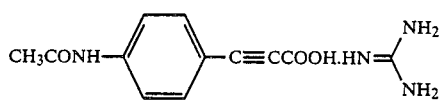 *3

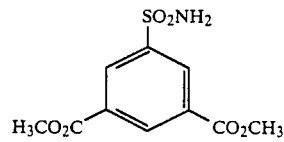 *4

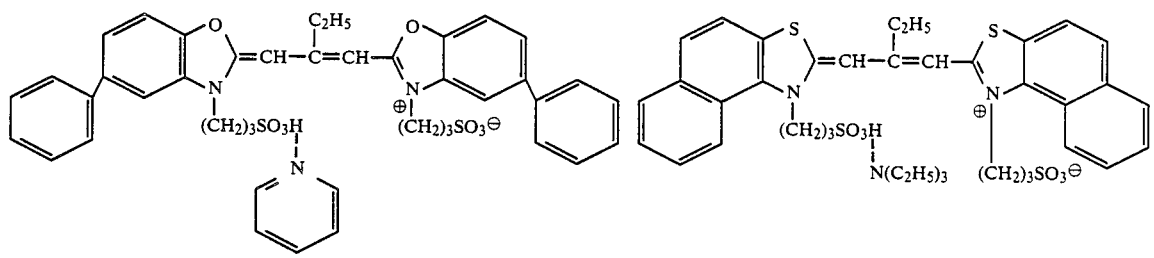

Then, the light-sensitive elements B and C were prepared by substituting the Compound (6) and Compound (10) according to the present invention for the Compound (3) in the light-sensitive element A. For control purposes, the light-sensitive element D free from the compound of the present invention was also prepared in the like manner.

The procedure for preparation of a dye fixing element having an image receiving layer is described below.

First, 0.75 g of gelatin hardener H-1, 0.25 g of gelatin hardener H-2 were evenly mixed with 160 ml of water and 100 g of 10% lime-treated gelatin. Then, a laminated polyethylene-paper support containing a dispersion of titanium oxide was evenly coated with the above mixture in a wet thickness of 60 μm, followed by drying.

Gelatin hardener H-1

Gelatin hardener H-2

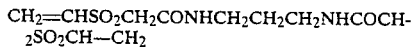

Then, 15 g of a polymer having the structure shown below was dissovled in 200 ml of water and the solution was mixed evenly with 100 g of 10% lime-treated gelatin. Then, this mixture was spread uniformly in a wet thickness of 85 μm in superimposition on the above layer, followed by drying. The product was used as a dye fixing element. Polymer

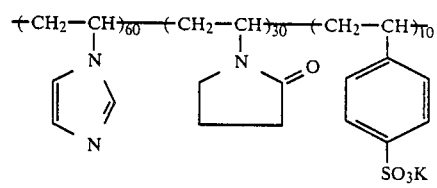

(Intrinsic viscosity 0.3473; measured in 1/20 M $Na_2HPO_4$ in water at 30° C.)

The above multi-layer color photographic light-sensitive element was exposed with tungsten light at 2,000 lux for 10 seconds through blue (B), green (G) and red (R) tricolor filters with continuous density variation, and then uniformly heated on a heat block at 150° C. or 153° C. for 20 seconds.

The image-receiving elements were immersed in water, and then the above heated light-sensitive elements A to D were respectively superimposed on the image-receiving elements with the effective layers facing each other.

After heating on a heat block at 80° C. for 6 seconds, the image-receiving element was separated from the light-sensitive element, whereby a negative magenta color image was obtained on the image receiving element. The density of this negative image was measured with a Macbeth reflection densitometer RD-519. The results are set forth in Table 1.

TABLE 1

| Sample No. | Compound No. of this invention | Filter | Heating at 150° C. for 20 sec. | | Heating at 153° C. for 20 sec. | |
|---|---|---|---|---|---|---|
| | | | Max. density | Min. density | Max. density | Min. density |
| A (The invention) | (3) | B | 1.90 | 0.14 | 1.93 | 0.16 |
| | | G | 1.98 | 0.14 | 2.00 | 0.17 |
| | | R | 2.05 | 0.15 | 2.08 | 0.19 |
| B (The invention) | (6) | B | 1.95 | 0.18 | 1.99 | 0.21 |
| | | G | 2.02 | 0.18 | 2.06 | 0.20 |
| | | R | 2.09 | 0.17 | 2.11 | 0.19 |
| C (The invention) | (10) | B | 1.92 | 0.15 | 1.96 | 0.19 |
| | | G | 2.00 | 0.18 | 2.04 | 0.22 |
| | | R | 2.08 | 0.16 | 2.10 | 0.19 |
| D (Control) | None | B | 1.95 | 0.18 | 2.03 | 0.31 |
| | | G | 2.04 | 0.20 | 2.16 | 0.41 |
| | | R | 2.12 | 0.17 | 2.30 | 0.29 |

It will be apparent from Table 1 that with the compound according to the present invention, the increases in maximum and minimum densities are small even when the development temperature is higher by 3° C. On the other hand, in the case of the control sample free from the compound of the present invention, fog is considerably increased. It is, thus, evident that the compound according to the present invention has a high temperature-complementing effect.

EXAMPLE 2

The procedure for preparation of a silver halide emulsion for the fifth layer is described below.

To a well-stirred aqueous solution of gelatin (20 g of gelatin and ammonia were dissolved in 1,000 cc of water and the solution was maintained at 50° C.), there were added an aqueous solution containing potassium iodide and potassium bromide (1,000 ml) and a solution of silver nitrate (1 mole of silver nitrate dissolved in 1,000 ml of water) concurrently white pAg was maintained constant, to provide a monodisperse octahedral silver iodobromide emulsion (iodine content: 5 mol %) with a mean grain size of 0.5 μm.

After washing and desalting, 5 mg of chloro-auric acid (4H$_2$O) and 2 mg of sodium thiosulfate were added to carry out the gold-sulfur sensitization at 60° C. 60° C. The yield of the emulsion was 1.0 kg.

The procedure for preparation of an emulsion for the third layer is described below.

To a well-stirred aqueous solution of gelatin (20 g of gelatin and 3 g of sodium chloride were dissolved in 1,000 ml of water and the solution was held at 75° C.) were added an aqueous solution containing sodium chloride and potassium bromide (600 ml), an aqueous solution of silver nitrate (0.59 mole of silver nitrate in 600 ml of water) and the dye solution (I) described below over a period of 40 minutes, concurrently in constant appropriate portions. The above procedure provided a monodisperse cubic silver chlorobromide emulsion (bromine content: 80 mol %) having dye adsorbed thereto and with a mean grain size of 0.35 μm.

After washing and desalting, 5 mg of sodium thiosulfate and 20 mg of 4-hydroxy-6-methyl-1,3-3a,7-tetrazaindene were added for chemical sensitization at 60° C. The yield of the emulsion was 600 g.

cedure gave a monodispersive cubic silver chloro-bromide emulsion (bromine content: 80 mol %) having the dye adsorbed and with a mean grain size of 0.35 μm.

After washing and desalting, 5 mg of sodium thiosulfate and 20 mg of 4-hydroxy-6-methyl-1,3,3a,7-tetrazaindene were added for chemical sensitization at 60° C. The yield of the emulsion was 600 g.

The procedure for preparation of a benzotriazole silver emulsion is described below.

In 3,000 ml of water were dissolved 28 g of gelatin and 13.2 g of benzotriazole and the solution was stirred at a constant temperature of 40° C. To this solution was added a solution of 17 g of silver nitrate in 100 ml of water over a period of 2 minutes.

The pH of the above benzotriazole silver emulsion was adjusted to cause precipitation and the excess salt was removed. Then, the emulsion was adjusted to a pH of 6.0 to provide 400 g of benzotriazole silver emulsion.

A dispersion of the color donor compound was prepared in the same manner as Example 1.

Using the above, a multi-layer color light-sensitive element E was prepared on a support as described below.

The sixth layer: Layer containing 740 mg/m$^2$ of gelatin, and 250 mg/m$^2$ of a base precursor (A)*[3].

The fifth layer: Blue-sensitive emulsion layer containing a silver iodobromide emulsion (containing 5 mol% of iodine and 500 mg/m$^2$ of silver), 160 mg/m$^2$ of benzenesulfamide, 270 mg/m$^2$ of a base precursor (A)*[3], benzotriazole silver emulsion (300 mg/m$^2$ of silver), 400 mg/m$^2$ of Yellow Dye Donor (1), 1,200 mg/m$^2$ of gelatin, 700 mg/m$^2$ of high boiling point solvent*[1], and 70 mg/m$^2$ of a surfactant*[2].

The fourth layer: Intermediate layer containing 700 mg/m$^2$ of gelatin and 240 mg/m$^2$ of a base precursor (A)*[3].

The third layer: Green-sensitive emulsion layer containing a silver chlorobromide emulsion (containing 80 mol% of bromine, and 200 mg/m$^2$ of silver), 140 mg/m$^2$ of benzenesulfamide, a benzotriazole silver emulsion (100 mg/m$^2$ of silver), 210 mg/m$^2$ of a base precursor (A)*[3], 330 mg/m$^2$ of Magenta Dye Donor (2), 860 mg/m$^2$ of gelatin, 430 mg/m$^2$ of a high boiling point solvent*[1], and 60 mg/m$^2$ of a surfactant*[2].

The second layer: Intermediate layer containing 1,000

Dye solution (I)

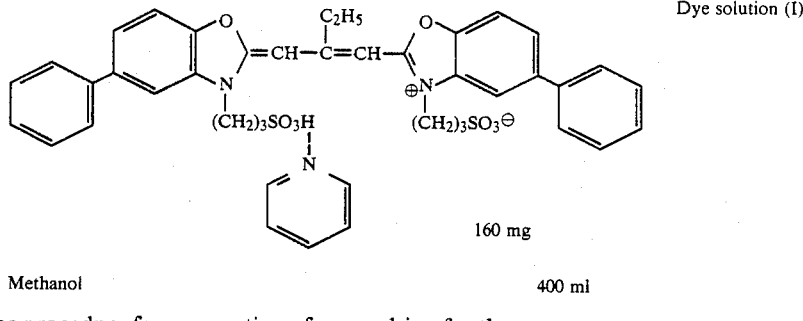

160 mg

Methanol          400 ml

The procedure for preparation of an emulsion for the first layer is described below.

To a well-stirred aqueous solution of gelatin (20 g of gelatin and 3 g of sodium chloride were dissolved in 1,000 ml of water and the solution was held at 75° C.) were added an aqueous solution containing sodium chloride and potassium bromide (600 ml) and an aqueous solution of silver nitrate (0.59 mole of silver nitrate in 600 ml of water) over a period of 40 minutes, concurrently in constant appropriate portions. The above promg/m$^2$ of gelatin, and 240 mg/m$^2$ of a base precursor (A)*[3].

The first layer: Red-sensitive emulsion layer containing a silver chlorobromide emulsion (containing 80 mol% bromine and 200 mg/m$^2$ of silver), 140 mg/m$^2$ of benzenesulfamide, $8 \times 10^{-7}$ mol/m$^2$ of Sensitizing Dye*[4], benzotriazole silver emulsion (230 mg/m$^2$ of silver), 230 mg/m$^2$ of a base precursor (A)*[3], 300 mg/m² of Cyan Dye Donor (3), 850 mg/m² of gelatin, 540 mg/m² of a high boiling paint solvent*¹, and 60 mg/m² of a surfactant*².

Ingredients employed therein are illustrated below.

*1 

*2 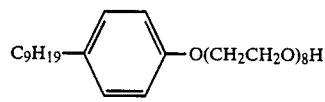

*3 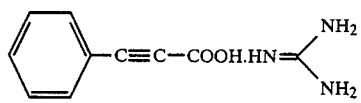

*4 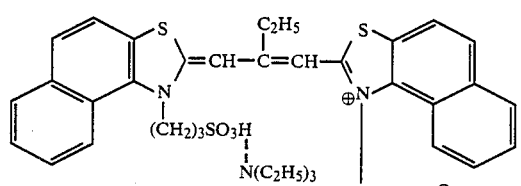

The procedure for preparation of the dye fixing element is described below

In 200 ml of water was dissolved 12 g of lime-treated gelatin followed by addition of 16 ml of a 0.5M aqueous solution of zinc acetate with stirring. The homogeneous mixture was then evenly coated on a 100 μm-thick white support of titanium dioxide-containing polyethylene terephthalate film in a wet thickness of 85 μm. On top of the resulting layer, the following coating composition was further coated in a wet thickness of 90 μm followed by drying to provide a dye fixing element.

| Dye fixing layer composition F: | |
|---|---|
| Polyvinyl alcohol (degree of polymerization: 2,000), 10% aqueous solution | 120 g |
| Urea | 20 g |
| N—methylurea | 20 g |
| ⁺CH₂—CH₎ₙ, 12% aqueous solution (intrinsic viscosity 0.1726, measured in aqueous NaCl at 30° C.) | 80 g |
| Compound (3) of the invention (described in Example 1) | 60 ml |
| Dye fixing layer composition G: | |
| Polyvinyl alcohol (degree of polymerization: 2,000), 10% aqueous solution | 120 g |
| Urea | 20 g |
| N—methylurea | 20 g |
| ⁺CH₂—CH₎ₙ, 12% aqueous solution | 80 g |

| -continued | |
|---|---|
| Water | 60 ml |

The above multi-layer color light-sensitive element was exposed with tungsten light at 2,000 lux for 1 second through the B, G, and R tricolor filters with continuous density variation and, then, uniformly heated on a heat block at 150° C. for 20 seconds.

This light-sensitive material was then laminated to the dye fixing element prepared above and after pressing and passage over a heat roller at 130° C., immediately heated on a heat block at 120° C. for 30 seconds. Immediately after heating, the dye fixing element was separated from the light sensitive element, whereupon yellow, magenta, and cyan-colored images were obtained in correspondence with the tricolor filters B, G, R on the dye fixing element. The maximum and minimum density values of each color were measured with a Macbeth reflection densitometer RD 519. The results are shown below.

TABLE 2

| Color filter | Dye fixing layer F (The invention) | | Dye fixing layer G (Comparison) | |
|---|---|---|---|---|
| | Max. density | Min. density | Max. density | Min. density |
| B | 1.87 | 0.20 | 1.90 | 0.28 |
| G | 2.11 | 0.17 | 2.12 | 0.32 |
| R | 2.20 | 0.18 | 2.25 | 0.29 |

It is clear from the above results that the incorporation of the compound according to the present invention in the dye fixing layer inhibits an increase of fog during the transfer process.

EXAMPLE 3

Ten grams of dye donor compound (4), 0.5 g of 2-ethylhexyl sodium sulfosuccinate and 10 g of tricresyl phosphate were weighed and 20 ml of cyclohexanone was added. The mixture was heated at 60° C. to provide a homogeneous solution. This solution was mixed with 100 g of a 10% aqueous solution of lime-treated gelatin with stirring and dispersed in a homogenizer.

Then, a light-sensitive element H was prepared in the following manner.

| (a) | The silver iodobromide emulsion of Example 1 | 5.5 g |
|---|---|---|
| (b) | 10% Aqueous gelatin solution | 0.5 g |
| (c) | The above dye donor compound dispersion | 2.5 g |
| (d) | Guanidine trichloroacetate, 10% in ethanol | 1 ml |
| (e) | 2,6-Dichloro-4-aminophenol, 10% in methanol | 0.5 ml |
| (f) | The following compound, 5% in water  | 1 ml |
| (g) | Compound (3) of the invention, dispersed in gelatin | 0.5 ml |
| (h) | Water | 6 ml |

-continued

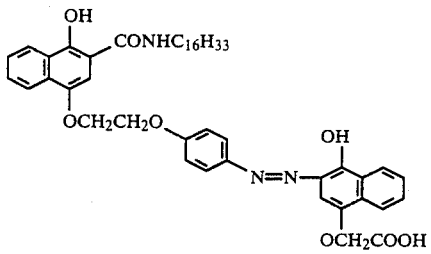

The above components (a) to (h) were mixed and dissolved by heating and the solution was coated on a polyethylene terephthalate film in a wet thickness of 85 μm.

On top of this layer was further coated a gelatin protective layer in a coverage of 1.5 g/m² to provide a light-sensitive element H. This light-sensitive element H was imagewise exposed with tungsten light at 2,000 lux for 10 seconds and evenly heated on a heat block at 140° C. or 143° C. for 30 seconds.

The above element was further subjected to the same procedure as Example 1. The results were as set forth in Table 3.

TABLE 3

|   | Heating at 140° C. for 30 sec. | | Heating at 143° C. for 30 sec. | |
|---|---|---|---|---|
|   | Max. density | Min. density | Max. density | Min. density |
| H | 2.02 | 0.18 | 2.04 | 0.20 |

The above results indicate that the effect of the compound according to the present invention is remarkable even in a photosensitive material containing a dye donor compound adapted to release a dye upon coupling with an oxidized developing agent.

EXAMPLE 4

To 5 g of a dye donor compound having the following structure (5), 4 g of an electron donor compound having the following structure, 0.5 g of 2-ethylhexyl sodium sulfosuccinate, and 10 g of tricresyl phosphate was added 20 ml of cyclohexanone and the mixture was heated at about 60° C. The resulting solution was thereafter treated in the same manner as Example 3, to provide a reducible dye donor compound dispersion.

Dye donor compound (5)

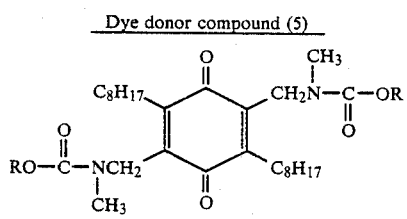

-continued

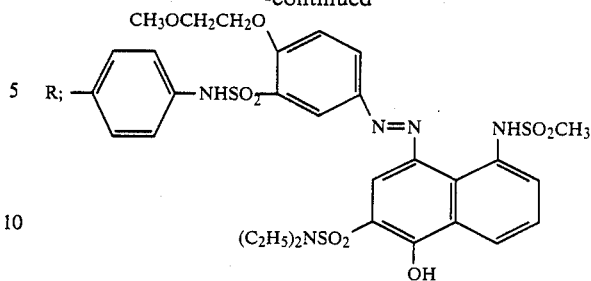

Electron donor compound

The procedure of Example 3 was repeated except the above-mentioned reducible dye donor dispersion was used in lieu of the dye donor (4) dispersion in the light-sensitive element (H) to provide a light-sensitive element (I).

This light-sensitive element was exposed and processed in the same manner as Example 3. The results are shown below.

TABLE 4

|   | Heating at 140° C. for 30 sec. | | Heating at 143° C. for 30 sec. | |
|---|---|---|---|---|
|   | Max. density | Min. density | Max. density | Min. density |
| I | 1.78 | 0.18 | 1.82 | 0.21 |

It is seen that the compound according to the present invention is also useful in a photosensitive material containing a reducible dye donor compound adapted to yield a positive image relative to the silver image.

EXAMPLE 5

Procedure for preparation of a gelatin dispersion of the coupler

Five grams of 2-dodecylcarbamoyl-1-naphthol, 0.5 g of 2-ethylhexyl sodium sulfosuccinate and 2.5 g of tricresyl phosphate (TCP) were weighed and 30 ml of ethyl acetate was added. The resulting solution was mixed with 100 g of a 10% solution of gelatin and dispersed in a homogenizer at 10,000 rpm for 10 minutes.

A light-sensitive element J was prepared in the following manner.

| (a) | Silver iodobromide emulsion (The emulsion of Example 1) | 10 g |
| (b) | Gelatin dispersion of coupler | 3.5 g |
| (c) | 0.25 g of Guanidine trichloroacetate dissolved in 2.5 cc of ethanol | 2.5 cc |
| (d) | Gelatin (10% aqueous solution) | 5 g |
| (e) | 2,6-Dichloro-p-aminophenol (dissolved in 15 cc of water) | 0.2 g |
| (f) | Gelatin dispersion of Compound (3) of the invention (as described | 1 ml | in Example 1)

The above composition was coated on a polyethylene terephthalate support in a wet thickness of 60 μm followed by drying to provide a light-sensitive element.

This light-sensitive element was imagewise exposed with tungsten light at 2,000 lux for 5 seconds. Then, the exposed element was uniformly heated on a heat block at 150° C. or 153° C. for 20 seconds, whereupon a negative cyan color image was obtained. The density of the color was measured with a Macbeth transmittance densitometer TD-504. The results were as follows.

TABLE 5

|   | Heating at 150° C. for 20 sec. | | Heating at 153° C. for 20 sec. | |
|---|---|---|---|---|
|   | Max. density | Min. density | Max. density | Min. density |
| J | 2.05 | 0.21 | 2.08 | 0.24 |

It is apparent that the compound according to the present invention has a high temperature complementing effect.

EXAMPLE 6

An example of the invention in black-and-white photography is given below.

A light-sensitive element K was prepared in the following manner.

| (a) | Silver iodobromide emulsion (the emulsion of Example 1) | 1 g |
|---|---|---|
| (b) | Benzotriazole silver emulsion (the emulsion of Example 2) | 10 g |
| (c) | Guanidine trichloroacetate (10% in ethanol) | 1 cc |
| (d) | A compound of the following structural formula, 5% in methanol | 2 cc |

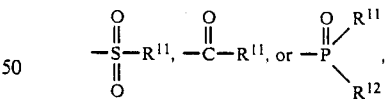

| (e) | Compound (3) of the invention, as dispersed in gelatin (described in Example 1) | 1 cc |

The above composition was coated on a polyethylene terephthalate support in a wet thickness of 60 μm, followed by drying.

The above light-sensitive element was imagewise exposed with tungsten light at 2,000 lux for 5 seconds. Then, the element was uniformly heated on a heat block at 130° C. or 133° C. for 30 seconds, whereupon a negative brown image was obtained. The density of the image was measured with a Macbeth transmission densitometer TD-504. The results are as follows.

TABLE 6

|   | Heating at 130° C. for 30 sec. | | Heating at 133° C. for 30 sec. | |
|---|---|---|---|---|
|   | Max. density | Min. density | Max. density | Min. density |
| K | 0.80 | 0.16 | 0.83 | 0.19 |

It is apparent that the compound according to the present invention has a remarkable high temperature-complementing effect.

While the invention has been described in detail and with reference to specific embodiments thereof, it will be apparent to one skilled in the art that various changes and modifications can be made therein without departing from the spirit and scope thereof.

What is claimed is:

1. An image forming process including heating a diazo or silver halide photographic material, which process comprises conducting said heating step in the presence of at least one compound represented by formula (I), (II), or (III)

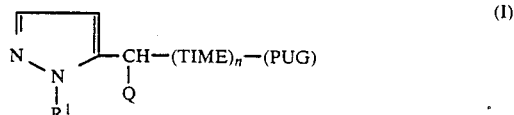

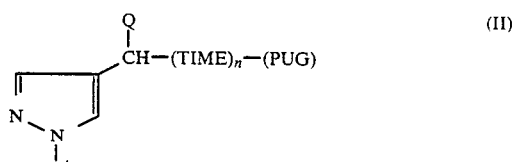

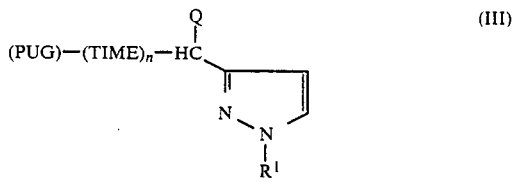

wherein $R^1$ represents $$-\underset{\underset{O}{\overset{O}{\|}}}{\overset{\|}{S}}-R^{11}, \quad -\overset{O}{\overset{\|}{C}}-R^{11}, \text{ or } -\overset{O}{\overset{\|}{P}}\diagup\overset{R^{11}}{\underset{R^{12}}{\diagdown}},$$

wherein $R^{11}$ and $R^{12}$ each represents a substituted or unsubstituted alkyl group, a substituted or unsubstituted cycloalkyl group, a substituted or unsubstituted alkenyl group, a substituted or unsubstituted aralkyl group, a substituted or unsubstituted aryl group, a substituted or unsubstituted heterocyclic group, a substituted or unsubstituted alkyloxy group, a substituted or unsubstituted aryloxy group, a substituted or unsubstituted alkylthio group, a substituted or unsubstituted arylthio group or a substituted or unsubstituted amino group, or $R^{11}$ and $R^{12}$ together form a 5-membered or 6-membered ring; Q represents a hydrogen atom or a substituted or unsubstituted alkyl group, a substituted or unsubstituted cycloalkyl group or a substituted or unsubstituted aryl group, or Q represents a group linked to the pyrazole ring, TIME, or PUG either directly or through another atom to form a ring; TIME represents a timing group; PUG represents a photographically useful group; and n represents 0 or a positive integer.

2. An image forming process as in claim 1, wherein said alkyl group represented by $R^{11}$ or $R^{12}$ is a straight-chain or branched-chain alkyl group having from 1 to 18 carbon atoms; said cycloalkyl group represented by $R^{11}$ or $R^{12}$ is a 5-membered or 6-membered cycloalkyl group having from 5 to 10 carbon atoms; said aryl group represented by $R^{11}$ or $R^{12}$ contains from 6 to 18 carbon atoms; said heterocyclic group represented by $R^{11}$ or $R^{12}$ is a 5-membered or 6-membered heterocyclic group wherein the hetero atom or atoms are selected from O, N, and S; said alkyloxy and aryloxy groups represented by $R^{11}$ or $R^{12}$ are represented by formula (D)

$$-OR^{13} \qquad (D)$$

wherein $R^{13}$ is a substituted or unsubstituted alkyl or substituted or unsubstituted aryl group as defined for $R^{11}$ and $R^{12}$; said alkylthio and arylthio groups represented by $R^{11}$ or $R^{12}$ are represented by formula (E)

$$-SR^{14} \qquad (E)$$

wherein $R^{14}$ is a substituted or unsubstituted alkyl or substituted or unsubstituted aryl group as defined for $R^{11}$ and $R^{12}$.

3. An image forming process as in claim 1, wherein Q representing an alkyl group as represented by $R^{11}$ or $R^{12}$ is a straight-chain or branched-chain alkyl group having from 1 to 18 carbon atoms; Q representing a cycloalkyl group is a 5-membered or 6-membered cycloalkyl group having from 5 to 10 carbon atoms; and Q representing an aryl group contains from 6 to 18 carbon atoms.

4. An image forming process as in claim 1, wherein the pryazole ring of formula (I), (II), or (III) is substituted with a substituted aryl group.

5. An image forming process as in claim 1, wherein the heating step is conducted at a temperature of from 60° to 180° C.

6. An image forming process as in claim 2, wherein the heating step is conducted at a temperature of from 60° to 180° C.

7. An image forming process as in claim 3, wherein the heating step is conducted at a temperature of from 60° to 180° C.

8. An image forming process as in claim 4, wherein the heating step is conducted at a temperature of from 60° to 180° C.

* * * * *